United States Patent
Ohmoto et al.

(10) Patent No.: US 8,716,490 B2
(45) Date of Patent: May 6, 2014

(54) COMPOUND HAVING DETRUSOR MUSCLE-CONTRACTING ACTIVITY AND URETHRAL SPHINCTER MUSCLE-RELAXING ACTIVITY

(71) Applicant: Ono Pharmaceutical Co., Ltd., Osaka (JP)

(72) Inventors: Kazuyuki Ohmoto, Osaka (JP); Akihiro Kinoshita, Osaka (JP); Hidekazu Matsuya, Osaka (JP); Hiroki Okada, Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 13/784,008

(22) Filed: Mar. 4, 2013

(65) Prior Publication Data

US 2013/0184236 A1  Jul. 18, 2013

Related U.S. Application Data

(63) Continuation of application No. 13/377,047, filed as application No. PCT/JP2010/059771 on Jun. 9, 2010, now Pat. No. 8,410,281.

(30) Foreign Application Priority Data

Jun. 10, 2009 (JP) ................. 2009-139657
Nov. 9, 2009 (JP) ................. 2009-256008

(51) Int. Cl.
*A61K 31/426* (2006.01)
*C07D 277/56* (2006.01)

(52) U.S. Cl.
USPC .......................... 548/188; 514/369

(58) Field of Classification Search
USPC ........................................... 548/188
See application file for complete search history.

(56) References Cited

U.S. PATENT DOCUMENTS

| | | | |
|---|---|---|---|
| 6,288,119 B1 | 9/2001 | Ohuchida et al. | |
| 7,402,605 B2 | 7/2008 | Tani et al. | |
| 2005/0020686 A1 | 1/2005 | Maruyama et al. | |
| 2005/0124577 A1 | 6/2005 | Tani et al. | |
| 2006/0109102 A1 | 5/2006 | Gortz et al. | |
| 2007/0129327 A1 | 6/2007 | Ohmoto et al. | |
| 2008/0021021 A1 | 1/2008 | Okada et al. | |
| 2009/0227644 A1 | 9/2009 | Ohmoto et al. | |

FOREIGN PATENT DOCUMENTS

| | | |
|---|---|---|
| EP | 0 156 611 A2 | 10/1985 |
| EP | 1 481 976 A1 | 12/2004 |
| EP | 1 586 564 A1 | 10/2005 |
| EP | 1 609 480 A1 | 12/2005 |
| EP | 1 707 208 A1 | 10/2006 |
| EP | 1 782 830 A1 | 5/2007 |
| EP | 1 806 148 A1 | 7/2007 |
| EP | 1 886 693 A1 | 2/2008 |
| JP | 11-130678 A | 5/1999 |
| WO | 03/009872 A1 | 2/2003 |
| WO | 03/074483 A1 | 9/2003 |
| WO | 2004/065365 A1 | 8/2004 |
| WO | 2004/089411 A1 | 10/2004 |
| WO | 2005/053707 A1 | 6/2005 |
| WO | 2005/061492 A1 | 7/2005 |
| WO | 2006/016689 A1 | 2/2006 |
| WO | 2006/043655 A1 | 4/2006 |
| WO | 2006/129788 A1 | 12/2006 |
| WO | 2009/148163 A1 | 12/2009 |

OTHER PUBLICATIONS

Takeda et al., Journal of Pharmacological Sciences, 112, pp. 121-127 (2010).*
International Searching Authority, International Search Report [PCT/ISA/210] issued by the International Searching Authority in International Application No. PCT/JP2010/059771 on Aug. 24, 2010.
Japanese Patent Office, Communication dated Mar. 29, 2011, issued by the Japanese Patent Office in counterpart Japanese Application No. 2011-503274.
Bilak et al., "PGE2 Receptors Rescue Motor Neurons in a Model of Amyotrophic Lateral Sclerosis," Annals of Neurology, 2004, vol. 56, No. 2, pp. 240 to 248, full test, particularly, p. 243, left column, line 48 to p. 244, line 11, Fig 3., abstract, lines 1 to 3.
H. Kuwada, "Effects of prostaglandin derivatives on changes of gastric mucosal protein contents in ethanol-induced ulcer", Cytoprotection & Biology, 1985, pp. 217-225, vol. 3.

(Continued)

*Primary Examiner* — Laura L. Stockton
(74) *Attorney, Agent, or Firm* — Sughrue Mion, PLLC

(57) ABSTRACT

Since a compound represented by formula (I) wherein all of the symbols are the same as defined in the specification, a salt thereof, a solvate thereof, a prodrug thereof, a mixture with a diastereomer thereof in an arbitrary ratio, or a cyclodextrin clathrate thereof have a contracting activity of bladder detrusor and a relaxing activity of urethral sphincter, they can ameliorate bladder contraction dysfunction and/or urethral relaxation dysfunction, and for example, are effective for underactive bladder. Additionally, the compound of the present invention has little risk of side effects on the urinary system, the circulatory system and the digestive system, and exhibits excellent pharmacokinetics, such as oral absorbability etc. Therefore, the compound of the present invention is useful as a superior agent for preventing, treating and/or ameliorating underactive bladder

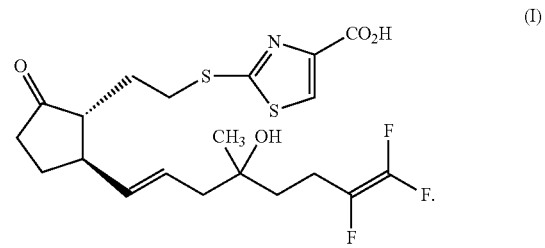

(I)

3 Claims, 6 Drawing Sheets

(56) References Cited

OTHER PUBLICATIONS

Kato et al., "Successful Treatment of Intermittent Claudication Due to Spinal Canal Stenosis Using Beraprost Sodium, a Stable Prostaglandin I2 Analogue," The Journal of Vascular Diseases, vol. 48, No. 5, pp. 457-461 (1997).

Kiyohiro Tsutsui, "Procylin Naifuku Toya go Soki Shita Livedo Kekkan'en no 1 Rei", The Journal of Medicine, 1994, pp. 611-613, vol. 32, No. 3.

Konno et al., "Effects of OP-1206 (Prostaglandin E1) on Nerve-Conduction Velocity in the Dog Cauda Equina Subjected to Acute Experimental Compression," Journal of Spinal Disorders, vol. 9, No. 2, pp. 103-106 (1996).

M. Kiriyama, "Ligand binding specificities of the eight types and subtypes of the mouse prostanoid receptors expressed in Chinese hamster ovary cells", 1997, pp. 217-224, vol. 122, No. 2.

Orendacova et al., "Cauda equina syndrome," Progress in Neurobiology, vol. 64, No. 6, pp. 613-637 (2001).

Y. Liu, "Rat Umao Shinkei Appaku Hoko Shogai Model Deno Beraprost Natrium to Limaprostal fadex Tono Hikaku", Basic Pharmacology & Therapeutics, 2002 pp. 875-880, vol. 30, No. 10.

Yone et al., "The effect of Lipo prostaglandin E1 on cauda equina blood flow in patients with lumbar spinal canal stenosis: myeloscopic observation," Spinal Cord, vol. 37, No. 4, pp. 269-274 (1999).

Stella et al., "Prodrugs: Challenges and Rewards, Part 1." Biotechnology: Pharmaceutical Aspects, p. 24, 2007.

Vippagunta et al. "Crystalline Solids." Advanced Drug Delivery Reviews, vol. 48, p. 3-26, 2001.

Chinese Patent Office, Chinese Office Action, Application No. 2006800286854; issued Jun. 9, 2010.

European Patent Office, European Office Action, Application No. 06756919.4; issued Jun. 10, 2010.

European Patent Office, Extended European Search Report for EP 06756919 dated Feb. 2, 2010.

International Searching Authority, International Search Report [PCT/ISA/210] issued in International Application No. PCT/JP2004/017961 on Feb. 1, 2005.

Israeli Patent Office, Israeli Office Action issued in Application No. 187840; dated Mar. 10, 2010.

New Zealand Patent Office, New Zealand Office Action, Application No. 563863; issued Jul. 1, 2010.

Russian Patent Office, Office Action in Russian Application No. 2007148992; issued Jun. 23, 2010.

European Patent Office, Supplementary European Search Report dated Feb. 12, 2010 in European Application No. 04819909.5.

U.S. Patent Office, U.S. Office Action issued Oct. 11, 2011 in counterpart U.S. Appl. No. 12/944,326.

U.S. Patent Office, Communication dated Sep. 17, 2012 issued in corresponding U.S. Appl. No. 12/889,731.

Jun Han, "Advances in Characterization of Pharmaceutical Hydrates", Trends in Bio/Pharmaceutical Industry, Mar. 2006, 6pgs total.

Karl-Erik Andersson, et al., "Pharmacology of the Lower Urinary Tract: Basis for Current and Future Treatments of Urinary Incontinence," Pharmacological Reviews, The American Society for Pharmacology and Experimental Therapeutics, vol. 56, No. 4, 2004, pp. 581-631.

European Patent Office, Extended European Search Report, dated Nov. 2, 2012, issued by the European Patent Office in counterpart European Patent Application No. 10786192.4.

Europeant Patent Office, European Office Action, dated Nov. 15, 2012, issued by the European Patent Office in counterpart European Patent Application No. 10786192.4.

A. D. Desmond, et al., "Clinical Experience with Intravesical Prostaglandin E2 A Prospective Study of 36 Patients," British Journal of Urology, British Association of Urological Surgeons, vol. 52, 1980, pp. 357-366.

Russian Patent Office, Office Action issued Jan. 29, 2014 in Russian Patent Application No. 2011152927.

"Chemical Encyclopedic Dictionary" Moscow, "Soviet encyclopedia", 1983, pp. 130-131.

M.D. Mashkovskiy, "Medicaments", Moscow, "Medicine", 2001, vol. 1, pp. 6-7.

Chinese Patent Office, Office Action issued Feb. 20, 2014 in Chinese Patent Application No. 201080035423.7.

* cited by examiner

US 8,716,490 B2

COMPOUND HAVING DETRUSOR MUSCLE-CONTRACTING ACTIVITY AND URETHRAL SPHINCTER MUSCLE-RELAXING ACTIVITY

CROSS-REFERENCE TO RELATED APPLICATIONS

The present application is a continuation of U.S. patent application Ser. No. 13/377,047 (now allowed), filed on Sep. 4, 2012, which is a National Stage Application of PCT/JP2010/059771, filed on Jun. 9, 2010, which claims the benefit of Japanese Patent Application No. 2009-256008, filed Nov. 9, 2009 and Japanese Patent Application No. 2009-139657, filed on Jun. 10, 2009. The entire disclosures of the prior applications are hereby incorporated by reference.

TECHNICAL FIELD

The present invention relates to a compound having a contracting activity of bladder detrusor and a relaxing activity of urethral sphincter, represented by formula (I):

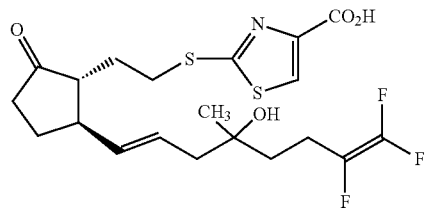

wherein all of the symbols have the same meanings as defined below, a salt thereof, a solvate thereof, a prodrug thereof, a mixture with a diastereomer thereof in an arbitrary ratio, or a cyclodextrin clathrate thereof (hereinafter, the compound represented by formula (I), the salt thereof, the solvate thereof, the prodrug thereof, the mixture with a diastereomer thereof in an arbitrary ratio, or the cyclodextrin clathrate thereof is also referred to simply as "compound of the present invention"). The present invention also relates to a pharmaceutical composition comprising the compound of the present invention as an active ingredient.

BACKGROUND ART

With regard to a symptom wherein bladder cannot be empty (incomplete bladder emptying) resulting from insufficient micturition contraction, a new terminology of underactive bladder has recently been proposed.

Underactive bladder is caused by bladder contraction dysfunction, i.e. a clinical condition wherein contractility of the bladder detrusor is decreased (detrusor underactivity), or a combination of urethral relaxation dysfunction (lower urinary tract passage dysfunction), i.e. a clinical condition with insufficient relaxation of the urethral sphincter and bladder contraction dysfunction, which is classified into neurogenic underactive bladder, myogenic underactive bladder, drug-induced underactive bladder, age-related underactive bladder, and underactive bladder induced by other factors (e.g., underactive bladder due to lower urinary tract obstruction, infection and stress etc.) depending on the causes.

Examples of causative diseases of neurogenic underactive bladder include: peripheral nerve disorders such as diabetes, disc hernia, spinal canal stenosis, Guillain-Barre syndrome, and herpes zoster-induced peripheral neuritis; spinal cord diseases, for example, supranuclear spinal cord injury, spinal cord tumor, cervical spondylosis, vascular diseases of the spinal cord, spina bifida, myelomeningocele and tethered cord syndrome; and brain diseases, such as dementia, cerebrovascular diseases, Parkinson's disease, spinocerebellar degeneration, olivopontocerebellar atrophy (OPCA), Shy-Drager syndrome, brain tumor, multiple sclerosis, cerebral trauma and encephalitis etc. In some cases, underactive bladder is caused by surgical injury of pelvic nerve, hypogastric nerve or pudendal nerve controlling voiding functions after surgical operations of pelvic viscera (uterine cancer or rectal cancer).

The myogenic underactive bladder is largely caused by a cryptogenic decreased activity of the bladder detrusor.

Examples of drug-induced underactive bladder include underactive bladder developed by anticholinergic drugs, drugs which inhibit release of acetylcholine and other factors.

Additionally, aged people generally exhibit dysuria caused by weakened bladder activity, and as a result, age-related underactive bladder becomes an important problem in an aging society.

Other examples of factors which cause underactive bladder include lower urinary tract obstruction caused by prostatic hyperplasia, bladder neck contracture or uterine prolapse, infections such as cystitis and urethritis, and stress (see Non-Patent Documents 1, 2 and 3).

For the treatment of underactive bladder, drugs which enhance the contractility of the bladder detrusor or reduce urethral resistance through the relaxation of the urethral sphincter are used. For example, cholinergic agents, such as bethanechol and acetylcholinesterase inhibitors, such as distigmine, are used as drugs for enhancing the contractility of the bladder detrusor. However, bethanechol also contributes to the contraction of the bladder detrusor at the urine collection period, which causes damage to the urine collection function of the bladder, and at the same time, has side effects such as lacrimation, perspiration, gastrointestinal disorders, abdominal pain etc. Therefore, it is contraindicated for pregnant women, and patients suffering with peptic ulcer, organic intestinal tract obstruction, asthma, hyperthyroidism etc. As acetylcholinesterase inhibitors, for example, distigmine and neostigmine, have been used. Since acetylcholinesterase inhibitors enhance the activity of acetylcholine released from the pelvic nerve endings in urination to enhance the contraction of the bladder detrusor in urination, they are considered excellent drugs when the physiological mechanism of micturition is taken into consideration. However, since distigmine contracts the bladder detrusor and also causes the contraction of the urethral sphincter due to a potent nicotine-like activity thereof to increase urethral resistance, voiding efficiency is not good and effects in terms of clinical application is insufficient. Additionally, the risk of high-pressure voiding has also been pointed out (see Non-Patent Document 4).

As drugs for relaxing the urethral sphincter and reducing urethral resistance, for example, α1 receptor antagonists, such as tamsulosin, prazosin, alfuzosin, naftopidil, urapidil etc. have been used and are reported that they are effective for the amelioration of subjective symptoms, such as feeling of residual urine and nocturia. However, since there are antihypertensive effects including orthostatic hypotension etc. as a side effect care should be taken for administration thereof. Additionally, there has been no report demonstrating satisfactory effects on underactive bladder.

Namely, drugs currently used for the treatment of underactive bladder are not clinically satisfactory in terms of therapeutic effects and safety.

On the other hand, Patent Document 1 discloses a compound for improving the blood flow in cauda equina nerve tissues, represented by formula (A):

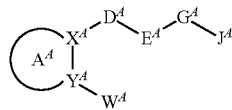

(A)

wherein the ring $A^A$ represents a 5- or 6-membered cyclic group which may contain 1 to 3 heteroatoms selected from nitrogen, oxygen and sulfur atoms or may further have substituents, $X^A$ and $Y^A$ each independently represent a nitrogen atom or a carbon atom, $D^A$ represents a hydrocarbon group which may have substituents, $E^A$ represents a bond, an oxygen atom, or a sulfur atom which may be oxidized, $G^A$ represents a bond, a hydrocarbon group which may have substituents or a heterocyclic group which may have substituents, $J^A$ represents an acidic group which may be protected, and $W^A$ represents a hydrocarbon group which may have substituents. Additionally, it is disclosed that the compound represented by formula (A) is effective for bladder disorder caused by cauda equina compression (see Patent Document 1.).

Additionally, a compound having a nerve regeneration or protection activity, represented by formula (B):

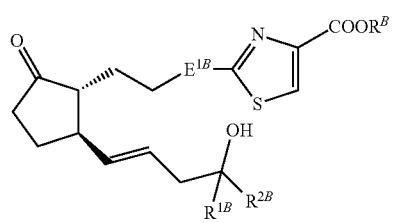

(B)

wherein $E^{1B}$ represents an oxygen atom or a sulfur atom which may be oxidized, $R^B$ represents a hydrogen atom or a $C_1$-$C_8$ aliphatic hydrocarbon group, $R^{1B}$ represents a hydrogen atom or a $C_1$-$C_4$ aliphatic hydrocarbon group, and $R^{2B}$ represents a hydrocarbon group which may have substituents is disclosed (see Patent Document 2.).

The compound of the present invention has not been disclosed in any literature.

Additionally, it is neither described nor suggested anywhere: the compound of the present invention acts on the bladder detrusor and urethral sphincter to enhance the contractility of the bladder detrusor and relax the urethral sphincter on the other hand; can ameliorate bladder contraction dysfunction or urethral relaxation dysfunction by the both activities; and exhibits effectiveness against underactive bladder, including myogenic, drug-induced, age-related etc. Additionally, it is neither described nor suggested that the compound of the present invention has little risk of side effects on the urinary system, the circulatory system and the digestive system; and has excellent pharmacokinetics, including oral absorbability, metabolic stability and efficacy duration.

PRIOR ART DOCUMENTS

Patent Documents

Patent Document 1: Pamphlet of International Publication No. WO 2005/053707

Patent Document 2: Pamphlet of International Publication No. WO 2006/129788

Non-Patent Documents

Non-Patent Document 1: Nursing Standard, 2005 May 11-17; 19(35): 57-64; quiz 66-7.

Non-Patent Document 2: Practice of Intractable and Chronic Dysuria, Urology View, vol. 2(5), pp 57-65, 2004

Non-Patent Document 3: The standardization of terminology in functions of lower urinary tract: report from the International Continence Society (ICS) Standardization Steering Committee, Journal of The Japan Neurogenic Bladder Society, vol. 14(2), pp 104-118, issued on Dec. 20, 2003

Non-Patent Document 4: Diagnosis and Therapy of Neurogenic Bladder, 2nd Ed., pp. 105-106, pp. 139, Igaku-Shoin Ltd. (1990).

SUMMARY OF THE INVENTION

Problems to be Solved by the Invention

Since cholinergic agents, acetylcholinesterase inhibitors and α1 receptor antagonists, which have been used for the treatment of underactive bladder, have only either of an activity for enhancing the contractility of the bladder detrusor or an activity for relaxing the urethral sphincter as the mechanisms of action thereof, they exhibit insufficient effects in terms of clinical application. Furthermore, since the drugs act on the autonomic nervous system, there has been pointed out the expression of side effects in organs other than the bladder.

Under such circumstances, there is a need for a drug that acts on smooth muscles involved in urination, particularly the bladder detrusor and the urethral sphincter, to contract the bladder and relax the urethra which achieves very high urination effects.

Since chronic diseases, such as underactive bladder, require long-term administration of drugs, there is a need for therapeutic agents which have little risk of side effects and can be administered orally when the safety and convenience of patients are taken into consideration.

Means for Solving the Problems

As a result of extensive research, the inventors of the present invention found that the compound of the present invention acts on two smooth muscles, i.e. the bladder detrusor and urethral smooth muscle, to exhibit surprising two activities of enhancing the contraction of the bladder detrusor and relaxing the urethral sphincter on the other hand, and can be provided as a very potent therapeutic agent for underactive bladder to ameliorate both bladder contraction dysfunction and urethral relaxation dysfunction. The inventors of the present invention also found that the compound of the present invention exhibits little risk of side effects on the urinary system, the circulatory system and the digestive system, and has excellent pharmacokinetics including oral absorbability, metabolic stability, efficacy duration etc. to accomplish the present invention.

Namely, the present invention relates to:
1. A compound represented by formula (I):

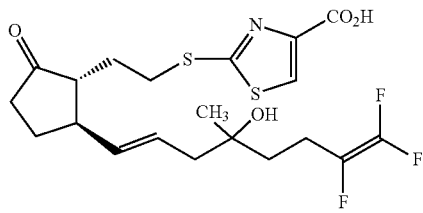

wherein ״‴ represents an α-configuration;
▰ represents a β-configuration; and
▱ represents an α-configuration, a β-configuration or an arbitrary mixture thereof, a salt thereof, a solvate thereof, a prodrug thereof, or a mixture with a diastereomer thereof in an arbitrary ratio, or a cyclodextrin clathrate thereof;

2. The compound of the above 1, wherein the compound is
(1)  2-[(2-{(1R,5R)-2-oxo-5-[(1E)-7,8,8-trifluoro-4-hydroxy-4-methyl-1,7-octadien-1-yl]cyclopentyl}ethyl) thio]-1,3-thiazole-4-carboxylic acid,
(2)  2-[(2-{(1R,5R)-2-oxo-5-[(1E,4S)-7,8,8-trifluoro-4-hydroxy-4-methyl-1,7-octadien-1-yl]cyclopentyl}ethyl) thio]-1,3-thiazole-4-carboxylic acid, or
(3)  2-[(2-{(1R,5R)-2-oxo-5-[(1E,4R)-7,8,8-trifluoro-4-hydroxy-4-methyl-1,7-octadien-1-yl]cyclopentyl}ethyl) thio]-1,3-thiazole-4-carboxylic acid;

3. The mixture in an arbitrary ratio of the above 1, wherein the compound is 2-[(2-{(1R,5R)-2-oxo-5-[(1E,4S)-7,8,8-trifluoro-4-hydroxy-4-methyl-1,7-octadien-1-yl] cyclopentyl}ethyl)thio]-1,3-thiazole-4-carboxylic acid and the diastereomer is 2-[(2-{(1S,5R)-2-oxo-5-[(1E,4S)-7,8,8-trifluoro-4-hydroxy-4-methyl-1,7-octadien-1-yl] cyclopentyl}ethyl)thio]-1,3-thiazole-4-carboxylic acid;

4. A pharmaceutical composition comprising, as an active ingredient, a compound represented by formula (I):

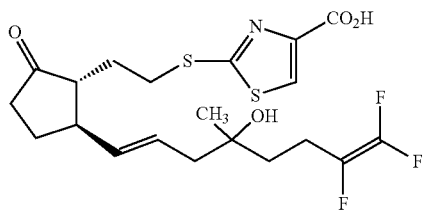

wherein all of the symbols have the same meanings as defined in the above 1, a salt thereof, a solvate thereof, a prodrug thereof, or a mixture with a diastereomer thereof in an arbitrary ratio, or a cyclodextrin clathrate thereof;

5. The pharmaceutical composition of the above 4, wherein the pharmaceutical composition is an agent for contracting the bladder detrusor and relaxing the urethral sphincter;

6. The pharmaceutical composition of the above 5, wherein the pharmaceutical composition is an agent for preventing, treating and/or ameliorating bladder contraction dysfunction and/or urethral relaxation dysfunction;

7. The pharmaceutical composition of the above 6, wherein the bladder contraction dysfunction and/or the urethral relaxation dysfunction is underactive bladder;

8. A medicament comprising a compound represented by formula (I):

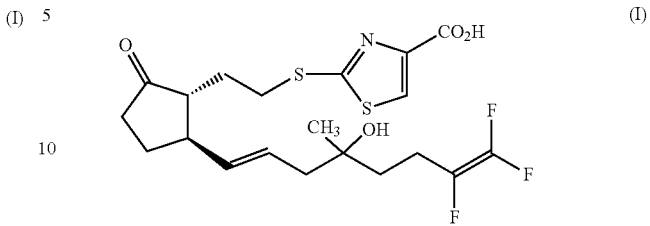

wherein all of the symbols have the same meanings as defined in claim 1, a salt thereof, a solvate thereof, a prodrug thereof, a mixture with a diastereomer thereof in an arbitrary ratio, or a cyclodextrin clathrate thereof, and at least one drug selected from α1 receptor antagonists and acetylcholinesterase inhibitors in combination;

9. A method for contracting the bladder detrusor and relaxing the urethral sphincter, comprising administering, to a mammal, an effective amount of a compound represented by formula (I):

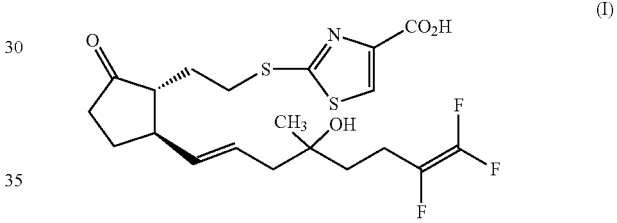

wherein all of the symbols have the same meaning as defined in 1, a salt thereof, a solvate thereof, a prodrug thereof, a mixture with a diastereomer thereof in an arbitrary ratio, or a cyclodextrin clathrate thereof;

10. A method for preventing, treating and/or ameliorating bladder contraction dysfunction and/or urethral relaxation dysfunction, comprising administering, to a mammal, an effective amount of a compound represented by formula (I):

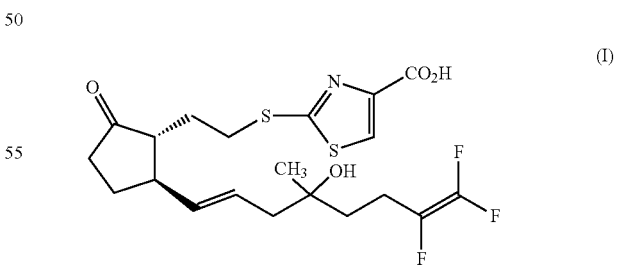

wherein all of the symbols have the same meaning as defined in 1, a salt thereof, a solvate thereof, a prodrug thereof, a mixture with a diastereomer thereof in an arbitrary ratio, or a cyclodextrin clathrate thereof;

11. Use of a compound represented by formula (I):

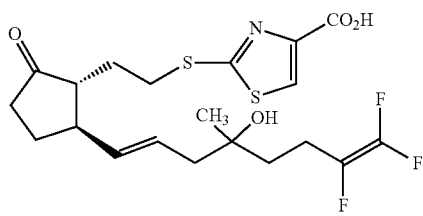

wherein all of the symbols have the same meaning as defined in 1, a salt thereof, a solvate thereof, a prodrug thereof, a mixture with a diastereomer thereof in an arbitrary ratio, or a cyclodextrin clathrate thereof, for the preparation of a bladder detrusor-contracting agent and a urethral sphincter-relaxing agent;

12. Use of a compound represented by formula (I):

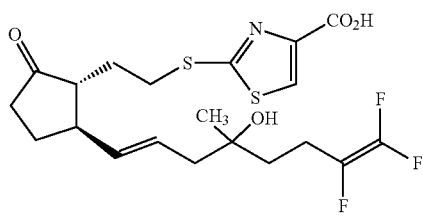

wherein all of the symbols have the same meaning as defined in 1, a salt thereof, a solvate thereof, a prodrug thereof, a mixture with a diastereomer thereof in an arbitrary ratio, or a cyclodextrin clathrate thereof, for the preparation of an agent for preventing, treating and/or ameliorating bladder contraction dysfunction and/or urethral relaxation dysfunction;

13. A compound represented by formula (I):

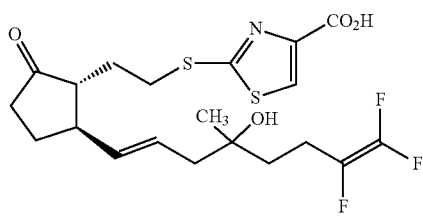

wherein all of the symbols have the same meaning as defined in 1, a salt thereof, a solvate thereof, a prodrug thereof, a mixture with a diastereomer thereof in an arbitrary ratio, or a cyclodextrin clathrate thereof, for contracting the bladder detrusor and relaxing the urethral sphincter; and 14. A compound represented by formula (I):

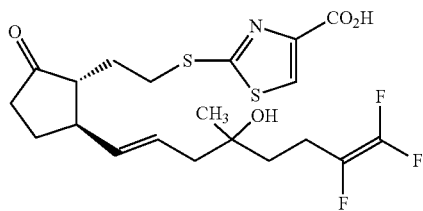

wherein all of the symbols have the same meaning as defined in 1, a salt thereof, a solvate thereof, a prodrug thereof, a mixture with a diastereomer thereof in an arbitrary ratio, or a cyclodextrin clathrate thereof, for preventing, treating and/or ameliorating bladder contraction dysfunction and/or urethral relaxation dysfunction.

Effects of the Invention

The compound of the present invention has a contracting activity of bladder detrusor and a relaxing activity of urethral sphincter. Therefore, the compound of the present invention can be used to ameliorate bladder contraction dysfunction and/or urethral relaxation dysfunction. Thus, the compound of the present invention is effective as an agent for preventing and/or treating underactive bladder. Additionally, the compound of the present invention is effective as an agent for ameliorating various symptoms associated with underactive bladder.

The compound of the present invention has little risk of side effects on the urinary system. For example, the compound of the present invention exhibits no storage symptom, such as bladder capacity reduction offering a high risk to patients suffering with urological diseases, in an effective dose.

Since the compound of the present invention causes little changes in blood pressure or heart rate on high-dose administration as well as at an effective dose, the compound of the present invention has little risk of side effects in patients suffering from circulatory diseases, such as hypertension. Therefore, the compound of the present invention has little effect on the cardiac function.

The compound of the present invention does not exhibit side effects on the digestive system, for example, digestive symptoms, such as diarrhea, in administration at an effective dose.

The compound of the present invention has a good membrane permeability and superior oral absorbability.

The compound of the present invention is stable against hepatic metabolism and has a low systemic clearance. Therefore, the compound of the present invention can exert sustained drug efficacy.

As described above, the compound of the present invention has very potent urination effects, high safety, and superior pharmacokinetics.

MODE FOR CARRYING OUT THE INVENTION

Figure 1:
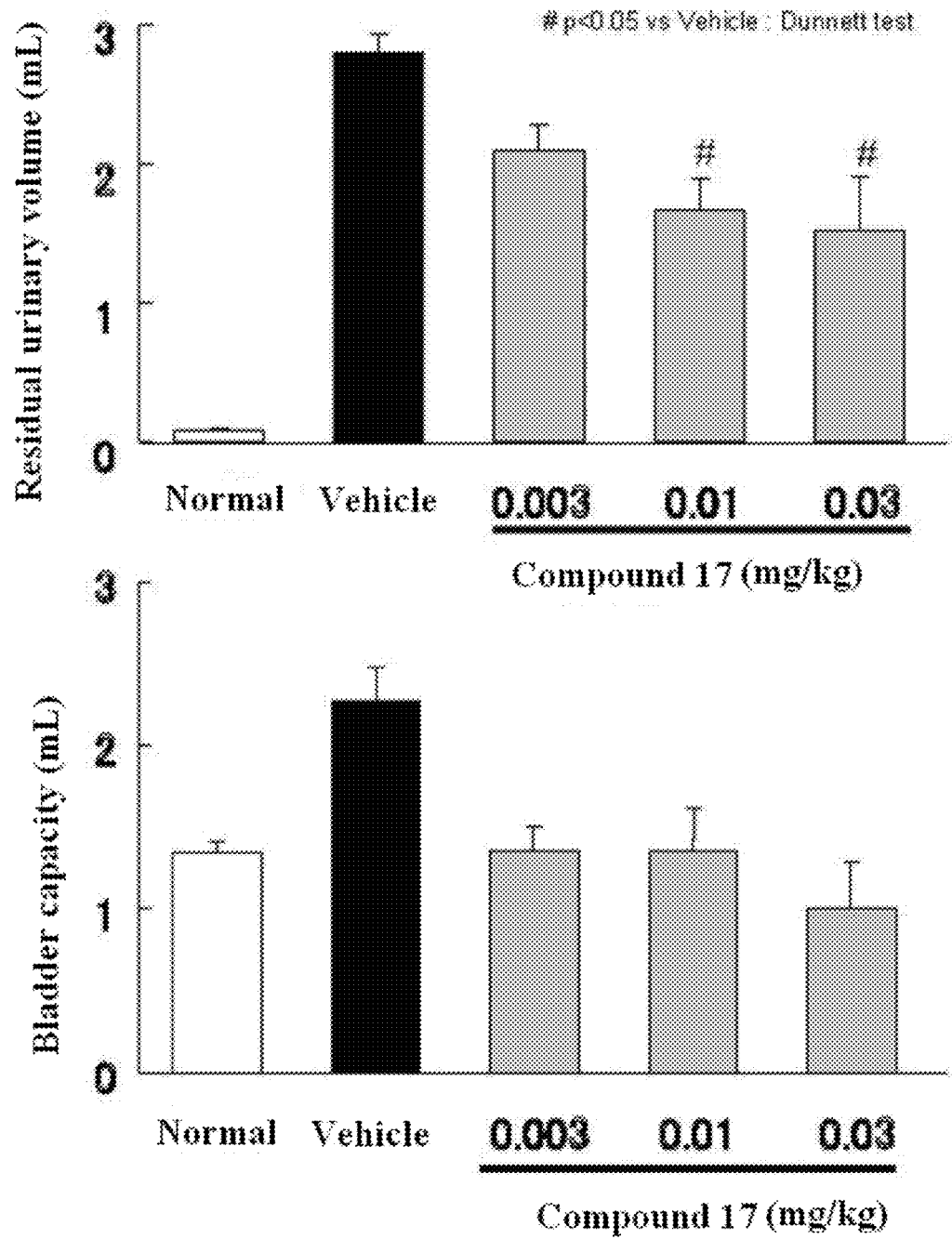
FIG. 1 shows the effect of the compound of the present invention on residual urinary volume (upper graph) and bladder capacity (lower graph) in underactive bladder models.

The present invention relates to a compound represented by formula (I):

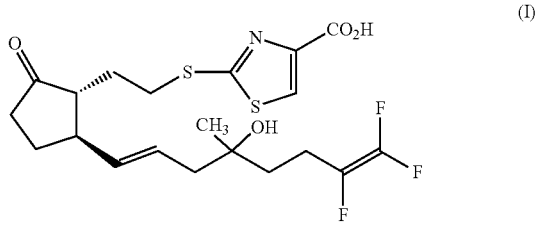 [SMILES: CC(O)(C/C=C/[C@H]1CCC(=O)[C@@H]1CCSc1nc(C(=O)O)cs1)CCC(F)=C(F)F]

(I)

wherein all of the symbols have the same meanings as defined above; a salt thereof, a solvate thereof, a prodrug thereof, a mixture with a diastereomer thereof in an arbitrary ratio, or a cyclodextrin clathrate thereof, and a pharmaceutical composition comprising the compound of the present invention as an active ingredient.

Unless otherwise specifically indicated herein, it is apparent to those skilled in the art that the symbol ⋯ represents a binding to the far side of the paper (i.e. α-configuration); the symbol ⁄ represents a binding to the front of the paper (i.e. β-configuration); and the symbol ╱ represents α-configuration, β-configuration or a mixture thereof.

As the compound of the present invention,
(1) 2-[(2-{(1R,5R)-2-oxo-5-[(1E)-7,8,8-trifluoro-4-hydroxy-4-methyl-1,7-octadien-1-yl]cyclopentyl}ethyl)thio]-1,3-thiazole-4-carboxylic acid,
(2) 2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylic acid, or
(3) 2-[(2-{(1R,5R)-2-oxo-5-[(1E,4R)-7,8,8-trifluoro-4-hydroxy-4-methyl-1,7-octadien-1-yl]cyclopentyl}ethyl)thio]-1,3-thiazole-4-carboxylic acid is preferable. Specifically, 2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylic acid (Compound 17) described in Example 17 is preferable.

As a salt, a water-soluble one is preferable. Examples of suitable salts include salts of alkali metals (for example, potassium, sodium etc.), salts of alkaline-earth metals (for example, potassium, magnesium etc.), ammonium salts, salts of pharmaceutically acceptable organic amines (for example, tetramethylammonium, triethylamine, methylamine, dimethylamine, cyclopentylamine, benzylamine, phenethylamine, monoethanolamine, diethanolamine, tris(hydroxymethyl)aminomethane, lysine, arginine and N-methyl-D-glucamine etc.) and acid-addition salts.

The acid-addition salts are preferably water soluble ones. Examples of suitable acid-addition salts include inorganic acid salts, such as hydrochlorides, hydrobromides, hydroiodides, sulfates, phosphates and nitrates; and organic acid salts, such as acetates, lactates, tartarates, benzoates, citrates, methanesulfonates, ethanesulfonates, benzenesulfonates, toluenesulfonates, isethionates, glucuronates and gluconates.

The compound represented by formula (I) and salts thereof may also be converted to corresponding solvates by any suitable methods.

It is preferable that the solvate is a low-toxicity and water-soluble one. Examples of suitable solvates include solvates of water and alcohols (for example, ethanol etc.).

The prodrug of the compound represented by formula (I), the salt thereof or the solvate thereof refers to a compound that is converted in vivo to the compound represented by formula (I), the salt thereof or the solvate thereof, for example, by enzymatic reactions and reactions with gastric acid. The prodrug of the compound represented by formula (I), the salt thereof or the solvate thereof may be, for example, a compound in which the hydroxyl group of the compound represented by formula (I) is acylated, alkylated, phosphorylated or borated (for example, a compound in which the hydroxyl group of the compound represented by formula (I) is acetylated, palmitoylated, propanoylated, pivaloylated, succinylated, fumarylated or alanylated, dimethylaminomethylcarbonylated); or a compound in which the carboxyl group of the compound represented by formula (I) is esterified or amidated (for example, a compound in which the carboxyl group of the compound represented by formula (I) is methyl esterified, ethyl esterified, propyl esterified, isopropyl esterified, butyl esterified, isobutyl esterified, tert-butyl esterified, phenyl esterified, carboxymethyl esterified, dimethylaminomethyl esterified, pivaloyloxymethyl esterified, 1-{(ethoxycarbonyl)oxy}ethyl esterified, phthalidyl esterified, (5-methyl-2-oxo-1,3-dioxolen-4-yl)methyl esterified, 1-{[(cyclohexyloxy)carbonyl]oxy}ethyl esterified or methyl amidated). These compounds can be prepared by methods known in the art. The prodrug of the compound represented by formula (I) may be either a solvated or non-solvated form. The prodrug of the compound represented by formula (I) may be one that is converted to the compound represented by formula (I) under physiological conditions, as described in "Development of Medicines", Vol. 7, "Molecular Design", pp. 163-198, published by HirokawaShoten in 1990.

The compound represented by formula (I) may be labeled with an isotope (for example, $^2$H, $^3$H, $^{11}$C, $^{13}$C, $^{14}$C, $^{13}$N, $^{15}$N, $^{15}$O, $^{17}$O, $^{18}$O, $^{35}$S, $^{18}$F, $^{36}$Cl, $^{123}$I or $^{125}$I etc.).

The prodrug of the compound represented by formula (I), the salt thereof or the solvate thereof may be, for example, a compound represented by formula (I-a):

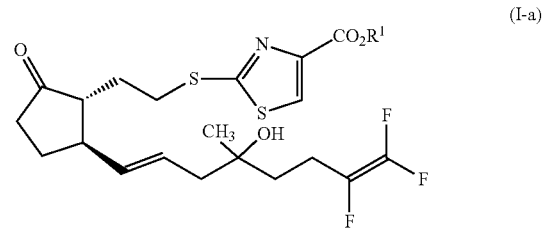

(I-a)

wherein $R^1$ represents a $C_1$-$C_4$ alkyl group, such as methyl, ethyl, propyl, isopropyl, butyl, isobutyl or tert-butyl etc., and the symbols have the same meanings as defined above.

The compound represented by formula (I), the salt thereof, the solvate thereof, the prodrug thereof or the mixture with a diastereomer thereof in an arbitrary ratio can be converted to a cyclodextrin clathrate using α-, β- or γ-cyclodextrin or a mixture thereof by any the methods described in the specifications of Japanese Patent Publication Nos. JP-B-S50-3362, JP-B-S52-31404 and JP-B-S61-52146. By converting into the cyclodextrin clathrate, since stability is increased and solubility in water is increased, the compound is convenient in case of use as a drug. The inclusion of the compound represented by formula (I), the salt thereof, the solvate thereof or the prodrug thereof in cyclodextrin can be determined by differential scanning calorimetry or powder X-ray diffraction analysis.

The present invention includes a diastereomer mixture of a diastereomer of the compound represented by formula (I) and the compound represented by formula (I) in an arbitrary ratio.

For example, there is 2-[(2-{(1S,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylic acid (Compound 20):

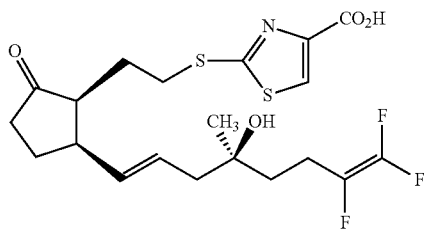 [SMILES: C[C@@](O)(C/C=C/[C@H]1CCC(=O)[C@H]1CCSc1nc(C(=O)O)cs1)CCC(F)=C(F)F]

as a diastereomer.

In this connection, as the mixture in an arbitrary ratio, the mixture wherein a ratio of the diastereomer thereof to the compound represented by the formula (I) is 1 to 20% based on the compound represented by formula (I) is preferable. The mixture wherein the ratio of the compound represented by formula (I): the diastereomer=9:1 is more preferable.

[Preparation Methods of the Compound of the Present Invention]

The compounds of the present invention can be prepared by appropriately modifying and combining methods known in the art, for example, methods described in the pamphlets of International Publication No. WO 2005/053707, International Publication No. WO 2006/129788 and Synlett 2002, No. 1, 239-242 and Comprehensive Organic Transformations: A Guide to Functional Group Preparations, 2nd Edition (Richard C. Larock, John Wiley & Sons Inc, 1999), methods shown below or methods shown in Examples.

For example, the compound represented by formula (I) can be prepared by subjecting a compound of Formula (II):

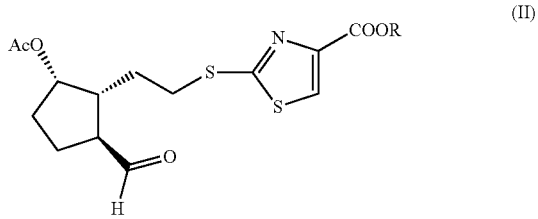

wherein Ac represents an acetyl group, R represents a protecting group for the carboxyl group (for example, a $C_1$-$C_4$ alkyl group, for example, methyl, ethyl, propyl, isopropyl, butyl, isobutyl or tert-butyl etc.), and a compound of formula (III):

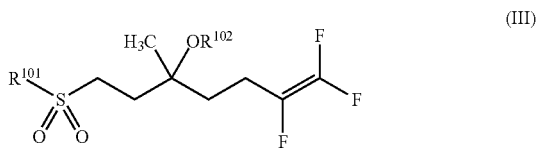

wherein $R^{101}$ represents an aryl group (for example, 1-phenyl-1H-tetrazolyl, phenyl etc.), $R^{102}$ is a protecting group (for example, trimethylsilyl, tert-butyldimethylsilyl etc.), to the following reactions, and further deprotecting and oxidizing the acetyl group, followed by deprotecting the protecting group.

The reactions between the compound represented by formula (II) and the compound represented by formula (III) are known. For example, the reaction is carried out in the presence of a base (for example, potassium hexamethyldisilazide, lithium diisopropylamide or butyl lithium etc.) in an organic solvent (for example, anhydrous tetrahydrofuran, dimethoxyethane, toluene or dimethylformamide etc.) at a temperature of about −100 to −20° C.

The deprotection reactions of the protecting groups, such as the acetyl group, are known in the art and can be carried out by the following procedure.

Examples of the protecting group for the carboxyl group include a $C_1$-$C_4$ alkyl group, such as methyl, ethyl, propyl, isopropyl, butyl, isobutyl or tert-butyl, an allyl group, a trichloroethyl group, a benzyl (Bn) group, a phenacyl group etc.

Examples of the protecting group for the hydroxyl group include methyl, trityl, methoxymethyl (MOM), 1-ethoxyethyl (EE), methoxyethoxymethyl (MEM), 2-tetrahydropyranyl (THP), trimethylsilyl (TMS), triethylsilyl (TES), tert-butyldimethylsilyl (TBDMS or TBS), tert-butyldiphenylsilyl (TBDPS), acetyl (Ac), pivaloyl, benzoyl, benzyl (Bn), p-methoxybenzyl, allyloxycarbonyl (Alloc) or 2,2,2-trichloroethoxycarbonyl (Troc) etc.

In addition to these protecting groups, any group that can be easily and selectively deprotected may be used as the protecting group for the carboxyl or hydroxyl group. For example, the protecting groups described in T. W. Greene, Protective Groups in Organic Synthesis, Wiley, New York, 1999 may be used.

The deprotection reactions of protecting groups for a carboxyl or hydroxyl group are well known in the art, for example:

(1) Deprotection by alkali hydrolysis,
(2) Deprotection under acid conditions,
(3) Deprotection by hydrogenolysis,
(4) Deprotection using silyl groups,
(5) Deprotection using metals, and
(6) Deprotection using metal complexes.

These methods will now be explained in detail.

(1) Deprotection by alkali hydrolysis is carried out, for example, using an alkali metal hydroxide (for example, sodium hydroxide, potassium hydroxide, lithium hydroxide etc.), an alkaline earth metal hydroxide (for example, barium hydroxide, calcium hydroxide etc.), a carbonate (for example, sodium carbonate, potassium carbonate etc.), an aqueous solution thereof, or a mixture thereof in an organic solvent (for example, methanol, tetrahydrofuran, dioxane etc.) at a temperature about 0 to about 40° C.

(2) Deprotection under acid conditions is carried out, for example, using an organic acid (for example, acetic acid, trifluoroacetic acid, methanesulfonic acid, p-tosylic acid etc.), an inorganic acid (for example, hydrochloric acid, sulfuric acid etc.) or a mixture thereof (for example, hydrogen bromide/acetic acid etc.) in an organic solvent (for example, dichloromethane, chloroform, dioxane, ethyl acetate, anisole etc.) at a temperature of about 0 to about 100° C.

(3) Deprotection by hydrogenolysis is carried out, for example, in a solvent (for example, an ether-based solvent (for example, tetrahydrofuran, dioxane, dimethoxyethane, diethyl ether etc.), an alcohol-based solvent (for example, methanol, ethanol etc.), a benzene-based solvent (for example, benzene, toluene etc.), a ketone-based solvent (for example, acetone, methyl ethyl ketone etc.), a nitrile-based solvent (for example, acetonitrile etc.), an amide-based solvent (for example, dimethylformamide etc.), water, ethyl acetate, acetic acid or a mixture solvent of two or more thereof) in the presence of a catalyst (for example, palladium-carbon, palladium black, palladium hydroxide, platinum oxide, Raney nickel etc.), in a hydrogen atmosphere or in the presence of ammonium formate under ambient pressure or under compression pressure at a temperature of about 0 to about 200° C.

(4) Deprotection using silyl groups may be carried out, for example, using tetrabutylammonium fluoride in an organic solvent (for example, tetrahydrofuran or acetonitrile etc.) which is miscible with water at a temperature of about 0 to about 40° C.

(5) Deprotection using metals may be carried out, for example, in an acidic solvent (for example, acetic acid, a buffer at a pH of about 4.2 to about 7.2, or a mixed solution thereof with an organic solvent such as tetrahydrofuran etc.) in the presence of zinc powder at a temperature of about 0 to about 40° C., if necessary, with sonication.

(6) Deprotection using metal complexes is carried out, for example, using a metal complex (for example, tetrakis(triphenylphosphine)palladium (0), bis(triphenylphosphine) palladium (II) dichloride, palladium (II) acetate or tris(triphenylphosphine)rhodium (I) chloride etc.) in an organic solvent (for example, dichloromethane, dimethylformamide, tetrahydrofuran, ethyl acetate, acetonitrile, dioxane or ethanol etc.), water or a mixed solvent thereof in the presence of a trapping reagent (for example, tributyltin hydride, triethylsilane, dimedone, morpholine, diethylamine or pyrrolidine etc.), an organic acid (for example, acetic acid, formic acid or 2-ethylhexanoic acid etc.) and/or an organic acid (for example, sodium 2-ethylhexanoate or potassium 2-ethylhexanoate etc.), with or without a phosphine reagent (for example, triphenylphosphine etc.), at a temperature of about 0 to about 40° C.

In addition to these, the deprotection reactions can also be carried out, for example, by the methods described in T. W. Greene, Protective Groups in Organic Synthesis, Wiley, New York, 1999.

Although it can be easily known by those skilled in the art, by selecting the deprotection reactions, the desired active ingredient of the present invention can be easily prepared.

The oxidation is known in the art and may be carried out, for example, using TEMPO reagent (2,2,6,6-tetramethylpiperidine 1-oxyl) and a reoxidant (aqueous hydrogen peroxide, sodium hypochlorite, 3-chloroperbenzoic acid, iodobenzene diacetate, potassium peroxymonosulfate (Oxone®) etc.) in an organic solvent (chloroform, dichloromethane, tetrahydrofuran, toluene, acetonitrile, ethyl acetate, water etc.) or a mixed solvent thereof in the presence or absence of a quaternary ammonium salt (tetrabutylammonium chloride, tetrabutylammonium bromide etc.), in the presence or absence of an inorganic salt (sodium bromide, potassium bromide etc.) or in the presence or absence of an inorganic base (sodium hydrogen carbonate, sodium acetate etc.) at a temperature of about −20 to about 60° C.

The compounds as starting raw materials in the reactions described in the present specification are known in the art or can be easily prepared by methods known in the art. For example, the compound represented by formula (II) can be prepared, for example, by the method described in the pamphlet of International Publication No. WO 2006/129788. The compound represented by formula (III) can be prepared, for example, by methods described in Examples described below.

The reactions described in the present specification can be carried out with using a water bath, oil bath, sand bath or microwave in case of reactions with heating, which is apparent to those skilled in the art.

In the reactions described in the present specification, a solid reagent contained in a polymer (for example, polystyrene, polyacrylamide, polypropylene and polyethylene glycol etc.) can be used appropriately.

In the reactions described in the present specification, the reaction products can be purified by general techniques, for example, distillation under ambient or reduced pressure, high-performance liquid chromatography using silica gel or magnesium silicate, thin layer chromatography, ion exchange resin chromatography scavenger resin chromatography, column chromatography, washing, recrystallization etc. The purification may be performed after each reaction or after several reactions.

[Toxicity]

The compound of the present invention causes less side effects and is thus safe enough to use as a drug.

[Applications to Medicaments]

The compound of the present invention acts on two smooth muscles, i.e. the bladder detrusor and the urethral sphincter, associated with underactive bladder. The compound of the present invention has the ability to enhance the contractility of the bladder detrusor and to relax the urethral sphincter on the other hand. Generally, drugs acting on smooth muscles induce the contraction for smooth muscles in anywhere if the drugs promote contraction or induce the relaxation for smooth muscles in anywhere if the drugs promote relaxation. There is not such compound as the compound of the present invention which promotes the contraction of some smooth muscles while it promotes the relaxation of other smooth muscles at the same time.

Since the compound of the present invention acts on smooth muscles, particularly the bladder detrusor and the urethral sphincter, to promote the contraction of the bladder detrusor and the relaxation of the urethral sphincter, it can ameliorate bladder contraction dysfunction and urethral relaxation dysfunction and is thus effective as an agent for preventing and/or treating underactive bladder. Additionally, the compound of the present invention is effective as an agent for ameliorating various symptoms associated with underactive bladder, for example, slow urine stream, split urine stream, blocked urine stream, delayed urination, abdominal pressure voiding, feeling of residual urine, overflow incontinence, anuresis and/or drop of urine after urination. The compound of the present invention is particularly effective as an agent for ameliorating split urine stream, blocked urine stream, abdominal pressure voiding, feeling of residual urine, overflow incontinence, anuresis and/or drop of urine after urination.

The compound of the present invention is also effective in preventing and/or treating spinal canal stenosis, cervical spondylosis, diseases of the peripheral nervous system, immune diseases (amyotrophic lateral sclerosis (ALS), multiple sclerosis, Sjogren's syndrome, chronic articular rheumatism, autoimmune diseases such as systemic erythematodes, rejection responses after organ transplantation, etc.), allergic diseases (for example, bronchial asthma, allergic nasal inflammation, allergic conjunctiva inflammation, atopic dermatitis, food allergy etc.), nerve cell death, dysmenorrhea, premature birth, misbirth, calvities, neural retinal diseases such as glaucoma, erectile dysfunction, arthritis, lung injury, fibroid lung, emphysema, bronchitis, chronic obstructive respiratory diseases, liver injury, acute hepatitis, cirrhosis, shock, nephritis (for example, acute nephritis, chronic nephritis etc.), renal dysfunction, pancreatitis, systemic inflammatory response syndrome, sepsis, hemophagocytic syndrome, macrophage activation syndrome, Still's disease, Kawasaki disease, burn injury, systemic granulomatous diseases, colitis ulcerosa, Crohn's disease, hypercytokinemia on dialysis, multiple organ dysfunction, bone diseases (bone fracture, refracture, intractable fracture, bone adhesion dysfunction, false joint, osteohalisteresis, bone Paget's disease, rigid spondylitis, cancer bone metastasis, arthrosis deformans, bone•cartilage breakdown in similar diseases thereof etc.).

The compound of the present invention and other drugs, it may be administered in combination with other drugs for the purpose of 1) supplementing and/or enhancing the prophylactic and/or therapeutic effects of the compound, 2) improving the pharmacokinetics and absorption of the compound, reducing the dose of the compound, and/or 3) alleviating the side effects of the compound.

With regard to the combination agent of the compound of the present invention and other drugs, it may be administered in combination with other drugs in the form of a blend in which the two ingredients are mixed in one preparation or in separate preparations. The administration of the two ingredients in separate preparations includes simultaneous administration and administration with a time interval. In administration with a time interval, it is possible that the compound of the present invention is administered in advance and the other drugs are administered later or it is possible that the other drugs are administered in advance and the compound of the present invention is administered later, wherein the administration modes of the two ingredients may be the same as or different from each other.

Examples of drugs suitable for supplementing and/or enhancing the effects of the compound of the present invention include acetylcholinesterase inhibitors (for example, distigmine and neostigmine etc.) and α1 acceptor antagonists (for example, tamsulosin, prazosin, alfuzosin, naftopidil, urapidil etc.).

There is no particular limitation on the weight ratio of the compound of the present invention to the other drugs.

The other drugs may be a combination of drugs of the same kind or two or more different kinds.

The other drug for supplementing and/or enhancing the effects of the compound of the present invention include not only currently found drugs and drugs which will be found based on the above mechanism.

In case where a combination agent of the compound of the present invention with the other drugs is used for the above purposes, it is usually adiministered systemically or locally, or orally or parenterally.

Although the dose may vary depending on the kind of the drug and may depend on age, weight, symptoms, intended therapeutic effects, administration methods, treatment time etc., the compound of the present invention may be usually administered orally at a dose ranging from 1 ng to 100 mg each time per an adult once or several times per day or, may be administered parenterally at a dose ranging from 0.1 ng to 10 mg each time per an adult once or several times per day or alternatively, may be continuously administered intravenously over a period of 1 to 24 hr per day.

Since the dose may vary depending on various conditions as described above, there is a case wherein the dose is sufficient with smaller amount than the dose described above while there is a case wherein administration with larger scope than the scope described above is necessary.

In case where the compound of the present invention or the combination agent of the compound of the present invention and other drug is administered, it may be used as internal solid preparations or internal liquid preparations for oral administration and injectables, external preparations, suppository and inhalations etc. for parenteral administration.

Examples of internal solid preparations suitable for oral administration includes tablets, pills, capsules, powders and granules. The capsules include hard capsules and soft capsules.

The internal solid preparations may be prepared using only one or more active ingredients or by mixing one or more active ingredients with for example, an excipient (lactose, mannitol, glucose, microcrystalline cellulose, starch etc.), a binder (hydroxypropyl cellulose, polyvinylpyrrolidone, alumina magnesium metasilicate etc.), a disintegrant (calcium carboxymethyl cellulose etc.), a lubricant (magnesium stearate etc.), a stabilizer or a dissolution aid (glutamic acid, asparaginic acid etc.) with formulation by techniques known in the art. If necessary, the solid preparations may be covered with a coating agent (for example, white sugar, gelatin, hydroxypropyl cellulose, hydroxypropyl methyl cellulose phthalate etc.) and may be covered with two or more layers. Capsules of absorbable materials, for example, gelatin, are also included.

Examples of internal liquid preparations suitable for oral administration include pharmaceutically acceptable aqueous solutions, suspending agents, emulsifying agents, syrups elixirs etc. In such a liquid preparation, one or more active substances are dissolved, suspended or emulsified in a diluent which is generally used in the art (for example, distilled water, ethanol, a mixed solution thereof etc.). The liquid preparations may contain a wetting agent, a suspending agent, an emulsifying agent, a sweetening agent, a flavoring agent, an aromatic agent, a preservative, a buffering agent, etc.

External formulations for parenteral administration include, for example, ointments, gels, creams, poultices, patches, liniments, aerosols, inhalations and sprays. Such a preparation includes one or more active substances and is prepared by methods known or commonly used in the art.

The ointments are prepared by methods known or commonly used in the art. For example, an ointment may be prepared by triturating or melting one or more active substances in a base. The ointment base is selected from those known or commonly used in the art. Examples of such ointment bases include higher fatty acids and higher fatty acid esters (adipic acid, myristic acid, palmitic acid, stearic acid, oleic acid, adipate, myristate, palmitate, stearate, oleate etc.), waxes (beeswax, hard wax, ceresin etc.), surfactants (polyoxyethylene alkyl ether phosphate etc.), higher alcohols (cetanol, stearyl alcohol, cetostearyl alcohol etc.), silicone oil (dimethylpolysiloxane etc.), hydrocarbons (hydrophilic Vaseline, white Vaseline, purified lanolin, liquid paraffin etc.), glycols (ethylene glycol, diethylene glycol, propylene glycol, polyethylene glycol, Macrogols etc.), vegetable oils (castor oil, olive oil, sesame oil, turpentine etc.), animal oils (mink oil, egg oil, squalane, squalene etc.), water, absorption accelerators, and anti-itch agents. These ointment bases may be used alone or as a mixture of two or more thereof. The ointments may further include a moisturizer, a preservative, a stabilizer, an antioxidant, a flavor, etc.

The gels are prepared by methods known or commonly used in the art. For example, a gel may be prepared by melting one or more active substances in a base. The gel base is selected from those known or commonly used in the art. Examples of such gel bases include lower alcohols (ethanol, isopropyl alcohol etc.), gelling agents (carboxymethyl cellulose, hydroxyethyl cellulose, hydroxypropyl cellulose, ethyl cellulose etc.), neutralizing agents (triethanolamine, diisopropanolamine etc.), surfactants (polyethylene glycol monostearate etc.), gums, water, absorption accelerators, and anti-itch agents. These gel bases may be used alone or as a mixture of two or more thereof. The gels may further include a preservative, an antioxidant, a flavor, etc.

The creams are prepared by methods known or commonly used in the art. For example, a cream may be prepared by melting or emulsifying one or more active substances in a base. The cream base is selected from those known or commonly used in the art. Examples of such cream bases include higher fatty acid esters, lower alcohols, hydrocarbons, polyhydric alcohols (propylene glycol, 1,3-butylene glycol, etc.), higher alcohols (2-hexyldecanol, cetanol etc.), emulsifiers (polyoxyethylene alkyl ethers, fatty acid esters etc.), water, absorption accelerators, and anti-itch agents. These cream bases may be used alone or as a mixture of two or more thereof. The creams may further include a preservative, an antioxidant, a flavor, etc.

The poultices are prepared by methods known or commonly used in the art. For example, a poultice may be prepared by melting one or more active substances in a base, kneading, followed by uniformly coating on a support. The poultice base is selected from those known or commonly used in the art. Examples of such poultice bases include thickeners (for example, polyacrylic acid, polyvinylpyrrolidone, arabic gum, starch, gelatin, methyl cellulose etc.), wetting agents (for example, urea, glycerin, propylene glycol etc.), fillers (kaolin, zinc oxide, talc, calcium, magnesium etc.), water, solubilizers, tackifiers, and anti-itch agents. These poultice bases may be used alone or as a mixture of two or more thereof. The poultices may further include a preservative, an antioxidant, a flavor, etc.

The patches are prepared by methods known or commonly used in the art. For example, a patch may be prepared by melting one or more active substances in a base and uniformly coating the melt on a support. The patch base is selected from those known or commonly used in the art. Examples of such patch bases include polymeric bases, oils and fats, higher fatty acids, thickeners, and anti-itch agents. These patch bases may be used alone or as a mixture of two or more thereof. The patches may further include a preservative, an antioxidant, a flavor, etc.

The liniments are prepared by methods known or commonly used in the art. For example, a liniment may be prepared by dissolving, suspending or emulsifying one or more active substances in one or more selected from water, alcohols (ethanol, polyethylene glycol etc.), higher fatty acids, glycerin, soaps, emulsifiers and suspending agents. The liniments may further include a preservative, an antioxidant, a flavor, etc.

The aerosols, inhalations and sprays may contain a stabilizer, such as sodium bisulfite or a buffering agent, for example, an isotonic agent such as sodium chloride, sodium citrate or citric acid, in addition to a diluent which is commonly used in the art.

The injectable preparations for parenteral administration may be, for example, solutions, suspensions, emulsions, and solid injectable preparations, which are dissolved or suspended in solvents in use. Such injectable preparation is used by dissolving, suspending or emulsifying one or more active substances in a solvent. Examples of suitable solvents include injectable distilled water, physiological saline, vegetable oils, propylene glycol, polyethylene glycol, alcohols such as ethanol, and combinations thereof. The injectable preparations may include stabilizers, dissolution aids (for example, glutamic acid, asparaginic acid, Polysolvate 80® etc.), suspending agents, emulsifying agents, soothing agents, buffers and preservatives. The injectable preparations are prepared by sterilization or disinfection in final steps. Aseptic solid preparations, for example, lyophilized solid preparations, can also be used by disinfecting or dissolving in aseptic injectable distilled water or other solvents before use.

Examples of the inhalations for parenteral administration include aerosols, powders for inhalation or liquids for inhalation. The liquids for inhalation may be dissolved or suspended in water or other proper medium before use.

The inhalations are prepared by methods known in the art. For example, a liquid for inhalation is prepared by selecting appropriately preservatives (benzalkonium chloride, paraben etc.), colorants, buffers (sodium phosphate, sodium acetate etc.), isotonic agents (sodium chloride, concentrated glycerin etc.), thickeners (carboxyvinyl polymer etc.) and absorbefacient, depending on the necessity.

A powder for inhalation is prepared by selecting appropriately lubricants (stearic acid, its salts etc.), binders (starch, dextrin etc.), excipients (lactose, cellulose etc.), colorants, preservatives (benzalkonium chloride, paraben etc.) and absorbefacient, depending on the necessity.

For administration of liquids for inhalation, sprayers (atomizers, nebulizers) are usually used. For administration of powders for inhalation, inhalators for the administration of powdery drugs are usually used.

Other compositions for parenteral administration include, one or more active substances and are for example, suppositories for intrarectal administration and pessaries for intravaginal administration.

EXAMPLES

The present invention will be explained in detail by Examples. However, the present invention is not limited by the Examples.

The solvents in the parenthesis indicated in the separated portion by the chromatography and TLC represent eluting or developing solvents used and their ratio is volume ratio.

NMR data are $^1$H-NMR data in 300 MHz unless otherwise specified. The parentheses in the NMR data represent solvents used for measurement.

The compounds used herein were named by a computer program which names chemical names according to the IUPAC rules, ACD/Name Batch (registered trademark), or according to IUPAC nomenclature. For example,

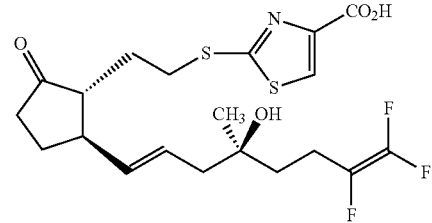 [SMILES: C[C@@](O)(C/C=C/[C@H]1CCC(=O)[C@@H]1CCSc1nc(C(=O)O)cs1)CCC(F)=C(F)F]

was named as 2-[(2-{(1R,5R)-2-oxo-5-[(1E,4S)-7,8,8-trifluoro-4-hydroxy-4-methyl-1,7-octadien-1-yl] cyclopentyl}ethyl)thio]-1,3-thiazole-4-carboxylic acid.

PREPARATION EXAMPLES

Example 1

4,5,5-trifluoro-N-methoxy-N-methyl-4-penteneamide (Compound 1)

N,O-dimethylhydroxyamine hydrochloride (3.5 g), 1-ethyl-3-(3-dimethylaminopropyl)carbodiimide hydrochloride (6.9 g) and triethylamine (9.2 mL) were added to a solution of 4,5,5-trifluoropent-4-enoic acid (CAS No. 110003-22-0 (5.0 g)) in methylene chloride solution (64 mL) in a cold-water bath and stirring was carried out at room temperature overnight. The reaction solution was concentrated and diluted with ethyl acetate. The dilute solution was washed with 1 N hydrochloric acid, water and saturated brine; dried with anhydrous sodium sulfate; and concentrated to obtain the title compound (6.4 g) having the following physical properties:

TLC: Rf 0.50 (ethyl acetate:hexane=1:2);
NMR (CDCl$_3$): δ 2.51-2.77 (m, 4H), 3.19 (s, 3H), 3.69 (s, 3H).

Example 2

Ethyl 6,7,7-trifluoro-3-oxo-6-heptenoate (Compound 2)

Ethyl acetate (4.8 mL) was slowly added dropwise to a lithium hexamethyldisilazide/tetrahydrofuran solution (1 M, 48 mL) at −78° C., followed by stirring for 30 min. The solution of compound 1 (6.4 g) in anhydrous tetrahydrofuran (33 mL) was slowly added dropwise to the reaction solution at the same temperature followed by stirring for 30 min. To the reaction solution, 2 N hydrochloric acid (30 mL) was added, followed by extraction with ethyl acetate. The organic layer was washed with water and saturated brine; dried with anhydrous sodium sulfate; and concentrated. The resulting residue was purified by silica gel column chromatography (hexane:ethyl acetate=20:1→15:1) to obtain the title compound (4.94 g) having the following physical properties:

TLC: Rf 0.63 (ethyl acetate:hexane=1:2);
NMR (CDCl$_3$): δ 1.29 (t, J=7.1 Hz, 3H), 2.50-2.71 (m, 2H), 2.83 (t, J=7.2 Hz, 2H), 3.47 (s, 2H), 4.21 (q, 2H).

Example 3

6,7,7-trifluoro-6-heptene-1,3-diol (Compound 3)

A solution of compound 2 (4.71 g) in tert-butyl methyl ether (52 mL) was slowly added dropwise to boron lithium hydride (1.4 g) under ice cooling, followed by stirring at room temperature for 4 hr. The reaction solution was poured into a saturated aqueous solution of ammonium chloride under ice cooling and washed with ethyl acetate. The organic layer was washed with saturated brine; dried with sodium sulfate; and concentrated to obtain the title compound (3.87 g) having the following physical properties:

TLC: Rf 0.31 (ethyl acetate:hexane=2:1);
NMR (CDCl$_3$): δ 1.66-1.83 (m, 4H), 2.17-2.66 (m, 2H), 3.71-4.06 (m, 3H).

Example 4

6,7,7-trifluoro-1-[(1-phenyl-1H-tetrazol-5-yl)thio]-6-hepten-3-ol (Compound 4)

Compound 3 (3.87 g) was dissolved in toluene (50 mL) and a 2N aqueous solution of sodium hydroxide (50 mL), and tetrabutylammonium bromide (700 mg) and tosyl chloride chloride (4.10 g) were added thereto under ice cooling, followed by stirring for 30 min. To the reaction solution 1-phenyl-1H-tetrazole-5-thiol (4.60 g) was added, followed by stirring at 60° C. overnight. The reaction solution was poured into water and extracted with tert-butyl methyl ether. The organic layer was washed with saturated brine; dried with sodium sulfate; and concentrated. The resulting residue was purified by silica gel column chromatography (hexane:ethyl acetate=4:1→7:3) to obtain the title compound (5.43 g) having the following physical properties:

TLC: Rf 0.37 (ethyl acetate:hexane=2:1);
NMR (CDCl$_3$): δ 1.64-1.83 (m, 2H), 1.88-2.02 (m, 2H), 2.31-2.61 (m, 2H), 3.34-3.88 (m, 3H), 7.46-7.69 (m, 5H).

Example 5

6,7,7-trifluoro-1-[(1-phenyl-1H-tetrazol-5-yl)thio]-6-hepten-3-one (Compound 5)

Potassium bromide (830 mg), 2,2,6,6-tetramethylpiperidine-1-oxyl (199 mg) and an aqueous solution of sodium hypochlorite (10%, 6.1 mL) were added to a acetonitrile solution (32 mL) of compound 4 (2.18 g) under ice cooling, followed by stirring for 2 hr. A saturated aqueous solution of sodium thiosulfate was added to the reaction solution at the same temperature, followed by extraction with ethyl acetate. The organic layer was washed with water and saturated brine; dried with anhydrous sodium sulfate; and concentrated to obtain the title compound (2.17 g) having the following physical properties:

TLC: Rf 0.50 (ethyl acetate:hexane=1:2);
NMR (CDCl$_3$): δ 2.48-2.77 (m, 4H), 3.14 (t, J=6.4 Hz, 2H), 3.57 (t, J=6.4 Hz, 2H), 7.54 (s, 5H).

Example 6

6,7,7-trifluoro-3-methyl-1-[(1-phenyl-1H-tetrazol-5-yl)thio]-6-hepten-3-ol (Compound 6)

A methyl magnesium bromide/diethyl ether solution (3.0 M, 4.2 mL) was added to an anhydrous tetrahydrofuran solution (22 mL) of compound 5 (2.17 g) at −78° C. The mixed solution was stirred for 30 min at the same temperature and for 30 min under ice cooling. A saturated aqueous solution of sodium hydrogen carbonate was added to the reaction solution under ice cooling, followed by extraction with ethyl acetate. The organic layer was washed with water and saturated brine; dried with anhydrous sodium sulfate; and concentrated. The resulting residue was purified by silica gel column chromatography (hexane:ethyl acetate=7:3) to obtain the title compound (1.88 g) having the following physical properties:

TLC: Rf 0.39 (ethyl acetate:hexane=1:2);
NMR (CDCl$_3$): δ 1.29 (s, 3H), 1.69-1.92 (m, 2H), 1.99-2.19 (m, 2H), 2.30-2.59 (m, 2H), 3.33-3.67 (m, 2H), 7.42-7.70 (m, 5H).

Example 7

6,7,7-trifluoro-3-methyl-1-[(1-phenyl-1H-tetrazol-5-yl)sulfonyl]-6-hepten-3-ol (Compound 7)

Hexaammonium heptamolybdenum tetrahydrate (318 mg) and aqueous hydrogen peroxide (30%, 1.8 mL) were added to a methanol solution (26 mL) of compound 6 (1.84 g) under ice cooling, followed by stirring at room temperature overnight. A saturated aqueous solution of sodium thiosulfate was added to the reaction solution under ice cooling, followed by extraction with ethyl acetate. The organic layer was washed with water and saturated brine; dried with anhydrous sodium sulfate; and concentrated to obtain the title compound (2.0 g) having the following physical properties:

TLC: Rf 0.41 (ethyl acetate:hexane=1:2);

NMR (CDCl$_3$): δ 1.30 (s, 3H), 1.69-1.86 (m, 2H), 2.06-2.24 (m, 2H), 2.30-2.57 (m, 2H), 3.80-4.00 (m, 2H), 7.51-7.78 (m, 5H).

Example 8

1-phenyl-5-({6,7,7-trifluoro-3-methyl-3-[(trimethyl-silyl)oxy]-6-hepten-1-yl}sulfonyl)-1H-tetrazole (Compound 8)

Imidazole (524 mg) and trimethylsilyl chloride (0.79 mL) were added to a solution of compound 7 (2.0 g) in dimethyl-formamide (11 mL) under ice cooling, followed by stirring at room temperature for 5 hr. The reaction solution was poured into water and extracted with ethyl acetate. The organic layer was washed with saturated brine; dried with anhydrous sodium sulfate; and concentrated. The resulting residue was purified by silica gel column chromatography (hexane:ethyl acetate=9:1) to obtain the title compound (2.16 g) having the following physical properties:
TLC: Rf 0.72(ethyl acetate:hexane=1:2);
NMR (CDCl$_3$): δ 0.15(s, 9H), 1.35 (s, 3H), 1.66-1.86 (m, 2H), 1.96-2.19 (m, 2H), 2.25-2.46 (m, 2H), 3.74-3.88 (m, 2H), 7.56-7.67 (m, 3H), 7.68-7.74 (m, 2H).

Example 9

Ethyl 2-({2-[(1R,2S,5S)-2-(acetyloxy)-5-formylcy-clopentyl]ethyl}thio)-1,3-thiazole-4-carboxylate (Compound 9)

Triethylamine (3.7 mL) and sulfur trioxide•pyridine complex (1.7 g) were added to a dimethyl sulfoxide (4.0 mL)/ethyl acetate (8.0 mL) solution of ethyl 2-({2-[(1R,2S,5S)-2-(acetyloxy)-5-(hydroxymethyl)cyclopentyl]ethyl}thio)-1,3-thiazole-4-carboxylate (500 mg) (see compound 7 described in the pamphlet of International Publication No. WO 2006/129788) at 10° C., followed by stirring at room temperature for 30 min. To the reaction solution, 1 N hydrochloric acid was added, followed by extraction with ethyl acetate. The organic layer was washed with water and saturated brine; dried with anhydrous sodium sulfate; and concentrated to obtain the title compound (497 mg) having the following physical properties:
TLC: Rf 0.27(hexane:ethyl acetate=2:1);
NMR (CDCl$_3$): δ 1.32-1.49 (m, 3H) 1.78-2.15 (m, 9H) 2.35-2.51 (m, 1H) 2.69-2.84 (m, 1H) 3.10-3.31 (m, 2H) 4.32-4.48 (m, 2H) 5.29-5.37 (m, 1H) 8.02 (s, 1H) 9.67 (d, J=2.74 Hz, 1H).

Example 10

Ethyl 2-{[2-((1R,2S,5R)-2-(acetyloxy)-5-{(1E)-7,8,8-trifluoro-4-methyl-4-[(trimethylsilyl)oxy]-1,7-octadien-1-yl}cyclopentyl]ethyl]thio}-1,3-thiazole-4-carboxylate (Compound 10)

A potassium hexamethyldisilazide/toluene solution (0.5 M, 4.8 mL) was slowly added dropwise to a 1,2-dimethoxy-ethane (8.0 mL) solution of compound 8 (1.13 g) at −78° C., followed by stirring at the same temperature for 30 min. To the reaction solution, a 1,2-dimethoxyethane solution (5.0 mL) of compound 9 (461 mg) in was slowly added dropwise at the same temperature. After string at the same temperature for 30 min, the temperature was raised to 0° C. A saturated aqueous solution of sodium hydrogen carbonate was added, followed by extraction with ethyl acetate. The organic layer was washed with water and saturated brine; dried with anhydrous sodium sulfate; and concentrated. The resulting residue was purified by silica gel column chromatography (hexane:ethyl acetate=8:1) to obtain the title compound (703 mg) having the following physical properties:
TLC: Rf 0.71(ethyl acetate:hexane=1:2);
NMR (CDCl$_3$): δ 0.10(s, 9H), 1.39 (t, J=7.1 Hz, 3H), 1.49-2.48 (m, 17H), 3.10-3.40 (m, 2H), 4.40 (q, J=7.1 Hz, 2H), 5.18-5.53 (m, 3H), 8.02 (s, 1H).

Example 11

2-[(2-{(1R,2S,5R)-2-hydroxy-5-[(1E)-7,8,8-trifluoro-4-hydroxy-4-methyl-1,7-octadien-1-yl]cyclopentyl}ethyl)thio]-1,3-thiazole-4-carboxylic acid (Compound 11)

To an ethanol solution (6.0 mL) of compound 10 (703 mg), 2 N aqueous solution of sodium hydroxide (2.4 mL) was added under ice cooling, followed by stirring at room temperature overnight. To the reaction solution, 1 N hydrochloric acid was added at the same temperature, followed by stirring for 30 min. Water was added to the reaction solution, followed by extraction with ethyl acetate. The organic layer was washed with saturated brine; dried with anhydrous sodium sulfate; and concentrated to obtain the title compound (538 mg) having the following physical properties:
TLC: Rf 0.21(ethyl acetate:methanol=5:1);
NMR (CDCl$_3$): δ 1.19(s, 3H), 1.32-1.50 (m, 2H), 1.61-1.92 (m, 4H), 1.94-2.56 (m, 8H), 2.81-2.99 (m, 1H), 3.49-3.67 (m, 1H), 4.56 (m, 1H), 5.27-5.62 (m, 2H), 8.08 (s, 1H).

Example 12

2-[(2-{(1R,2S,5R)-2-(acetyloxy)-5-[(1E)-7,8,8-trifluoro-4-hydroxy-4-methyl-1,7-octadien-1-yl]cyclopentyl}ethyl)thio]-1,3-thiazole-4-carboxylic acid (Compound 12)

Anhydrous acetic acid (0.33 mL) was added to a pyridine solution (6.0 mL) of compound 11 (538 mg) under ice cooling, followed by stirring at room temperature overnight. The reaction solution was poured into 1 N hydrochloric acid and extracted with ethyl acetate. The organic layer was washed with saturated brine; dried with anhydrous sodium sulfate; and concentrated to obtain the title compound (589 mg) having the following physical properties:
TLC: Rf 0.27(ethyl acetate:methanol=5:1);
NMR (CDCl$_3$): δ 1.16-1.21 (m, 3H), 1.34-2.54 (m, 17H), 3.10-3.53 (m, 2H), 5.33-5.61 (m, 3H), 8.11 (s, 1H).

Example 13

(10S,12E,13aR,16S,16aR)-10-methyl-8-oxo-10-(3,4,4-trifluoro-3-buten-1-yl)-1,10,11,13a,14,15,16,16a-octahydro-2H,8H-7,4-(azeno)cyclopenta[j][1,5,7]oxadithiacyclopentadecin-16-yl acetate (low-polarity form: compound 13A)

(10R,12E,13aR,16S,16aR)-10-methyl-8-oxo-10-(3,4,4-trifluoro-3-buten-1-yl)-1,10,11,13a,14,15,16,16a-octahydro-2H,8H-7,4-(azeno)cyclopenta[j][1,5,7]oxadithiacyclopentadecin-16-yl acetate (high-polarity form: compound 13B)

To a toluene solution (58 mL) of compound 12 (589 mg), 4,4-dimethylaminopyridine (567 mg) was added at room temperature. The reaction solution was heated to 100° C., and 2,4,6-trichlorobenzoyl chloride (0.37 mL) was added thereto. After stirring for 15 min, cooling to room temperature was carried out. The reaction solution was poured into a saturated aqueous solution of sodium hydrogen carbonate and extracted with ethyl acetate. The organic layer was washed with water and saturated brine; dried with anhydrous sodium sulfate; and concentrated. The resulting residue was purified by silica gel column chromatography (hexane:ethyl acetate=15:1) to obtain the title compounds (compound 13A: 200 mg, compound 13B: 120 mg) having the following physical properties:

Compound 13A

TLC: Rf 0.49 (ethyl acetate:hexane=1:4);
NMR (CDCl$_3$): δ 1.32-2.22 (m, 14H), 2.27-2.50 (m, 3H), 2.55-2.75 (m, 2H), 2.78-3.00 (m, 2H), 3.22-3.40 (m, 1H), 5.26-5.35 (m, 1H), 5.37-5.50 (m, 1H), 5.55-5.71 (m, 1H), 7.98 (s, 1H).

Compound 13B

TLC: Rf 0.46 (ethyl acetate:hexane=1:4);
NMR (CDCl$_3$): δ 1.32-2.61 (m, 19H), 2.80-3.01 (m, 2H), 3.18-3.32 (m, 1H), 5.26-5.36 (m, 1H), 5.44-5.69 (m, 2H), 7.96 (s, 1H).

Example 14

2-[(2-{(1R,2S,5R)-2-hydroxy-5-[(1E,4S)-7,8,8-trifluoro-4-hydroxy-4-methyl-1,7-octadien-1-yl]cyclopentyl}ethyl)thio]-1,3-thiazole-4-carboxylic acid (Compound 14)

Compound 13A (200 mg) was dissolved in a mixed solvent of methanol (1.0 mL) and tetrahydrofuran (2.0 mL), and a 2 N aqueous solution of sodium hydroxide (0.62 mL) was added, followed by stirring at room temperature overnight. The reaction solution was poured into 1 N hydrochloric acid and extracted with ethyl acetate. The organic layer was washed with water and saturated brine; dried with anhydrous sodium sulfate; and concentrated to obtain the title compound (190 mg) having the following physical properties:
TLC: Rf 0.21 (ethyl acetate:methanol=5:1);
NMR (CDCl$_3$): δ 1.19(s, 3H), 1.33-1.52 (m, 2H), 1.59-2.14 (m, 7H), 2.20 (d, J=6.6 Hz, 2H), 2.25-2.51 (m, 3H), 2.81-3.01 (m, 1H), 3.50-3.67 (m, 1H), 4.51-4.59 (m, 1H), 5.31-5.54 (m, 2H), 8.07 (s, 1H).

Example 15

Methyl 2-[(2-{(1R,2S,5R)-2-hydroxy-5-[(1E,4S)-7,8,8-trifluoro-4-hydroxy-4-methyl-1,7-octadien-1-yl]cyclopentyl}ethyl)thio]-1,3-thiazole-4-carboxylate (Compound 15)

Potassium carbonate (340 mg) and methyl iodide (0.09 mL) were added to a dimethylformamide solution (2.1 mL) of compound 14 (190 mg), followed by stirring at room temperature overnight. The reaction solution was poured into water and extracted with ethyl acetate. The organic layer was washed with water and saturated brine; dried with anhydrous sodium sulfate; and concentrated to obtain the title compound (196 mg) having the following physical properties:
TLC: Rf 0.36 (ethyl acetate:hexane=1:1);
NMR (CDCl$_3$): δ 1.18(s, 3H), 1.29-1.49 (m, 2H), 1.53-1.88 (m, 4H), 1.91-2.11 (m, 3H), 2.19 (d, J=6.2 Hz, 2H), 2.27-2.52 (m, 3H), 2.82-2.97 (m, 1H), 3.50-3.68 (m, 1H), 3.92 (s, 3H), 4.42-4.53 (m, 1H), 5.30-5.51 (m, 2H), 7.98 (s, 1H).

Example 16

Methyl 2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylate (Compound 16)

Diisopropylethylamine (0.43 mL) and sulfur trioxide•pyridine complex (196 mg) were added to a dimethyl sulfoxide (1.4 mL)/ethyl acetate (2.8 mL) solution of compound 15 (196 mg) under ice cooling, followed by stirring for 15 min. Water was added to the reaction solution, followed by extraction with ethyl acetate. The organic layer was washed with 1 N hydrochloric acid, water and saturated brine; dried with anhydrous sodium sulfate; and concentrated. The resulting residue was purified by silica gel column chromatography (hexane:ethyl acetate=3:2) to obtain the title compound (152 mg) having the following physical properties:
TLC: Rf 0.45(ethyl acetate:hexane=1:1);
NMR (CDCl$_3$): δ 1.16(s, 3H), 1.46-2.63 (m, 14H), 3.37-3.49 (m, 2H), 3.91 (s, 3H), 5.45-5.57 (m, 1H), 5.61-5.76 (m, 1H), 8.01 (s, 1H).

Example 17

2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylic acid (Compound 17)

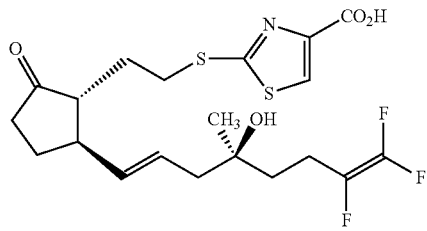 [SMILES: C[C@@](O)(C/C=C/[C@H]1CCC(=O)[C@@H]1CCSc1nc(C(=O)O)cs1)CCC(F)=C(F)F]

Compound 16 (152 mg) was dissolved in 1,2-dimethoxyethane (2.0 mL)/water (1.0 mL), and lithium hydroxide (16.0 mg) was added thereto under ice cooling, followed by stirring at room temperature for 2 hr. The reaction solution was poured into a 5% aqueous solution of potassium hydrogen sulfate and extracted with ethyl acetate. The organic layer was washed with water and saturated brine; dried with anhydrous sodium sulfate; and concentrated. The resulting residue was purified by silica gel column chromatography (hexane:ethyl acetate=1:1→methanol:ethyl acetate=1:10) to obtain the title compound (127 mg, amorphous, viscous oil) having the following physical properties:
TLC: Rf 0.20(ethyl acetate:methanol=5:1);

NMR (CDCl$_3$): δ 1.21(s, 3H), 1.55-1.80 (m, 3H), 1.88-2.60 (m, 11H), 3.37 (t, J=7.50 Hz, 2H), 5.54 (dd, J=14.82, 7.68 Hz, 1H), 5.62-5.76 (m, 1H), 8.11 (s, 1H).

Example 18

2-[(2-{(1R,5R)-2-oxo-5-[(1E,4R)-7,8,8-trifluoro-4-hydroxy-4-methyl-1,7-octadien-1-yl]cyclopentyl}ethyl)thio]-1,3-thiazole-4-carboxylic acid (Compound 18)

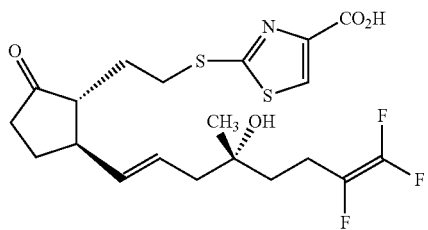 [SMILES: C[C@](O)(C/C=C/[C@H]1CCC(=O)[C@@H]1CCSc1nc(C(=O)O)cs1)CCC(F)=C(F)F]

The same procedure of Examples 14→15→16→17 was carried out except that compound 13B was used instead of compound 13A, to obtain the title compound (57.3 mg, amorphous, viscous oil).

TLC: Rf 0.20 (ethyl acetate:methanol=5:1);

NMR (CDCl$_3$): δ 1.21(s, 3H), 1.56-1.79 (m, 3H), 1.91-2.59 (m, 11H), 3.31-3.42 (m, 2H), 5.54 (dd, J=15.57, 8.04 Hz, 1H), 5.61-5.77 (m, 1H), 8.11 (s, 1H).

Example 19

2-[(2-{(1R,5R)-2-oxo-5-[(1E)-7,8,8-trifluoro-4-hydroxy-4-methyl-1,7-octadien-1-yl]cyclopentyl}ethyl)thio]-1,3-thiazole-4-carboxylic acid (Compound 19)

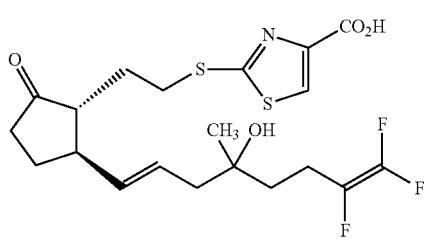 [SMILES: CC(O)(C/C=C/[C@H]1CCC(=O)[C@@H]1CCSc1nc(C(=O)O)cs1)CCC(F)=C(F)F]

The same procedure of Examples 15→16→17 was carried out except that compound 11 was used instead of compound 14, to obtain the title compound (7.6 mg, amorphous, viscous oil).

TLC: Rf 0.71(ethyl acetate:methanol:acetic acid=8:1:1);

NMR (CDCl$_3$): δ 1.21(s, 3H), 1.56-1.80 (m, 3H), 1.90-2.60 (m, 11H), 3.18-3.62 (m, 2H), 5.54 (dd, J=15.3, 7.8 Hz, 1H), 5.60-5.75 (m, 1H), 8.10 (s, 1H).

Example 20

2-[(2-{(1S,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylic acid (Compound 20)

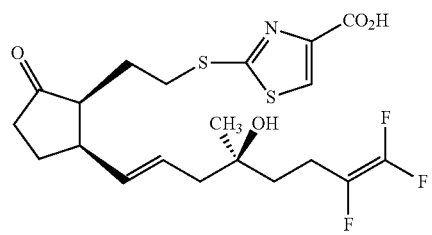 [SMILES: C[C@@](O)(C/C=C/[C@H]1CCC(=O)[C@H]1CCSc1nc(C(=O)O)cs1)CCC(F)=C(F)F]

TLC: Rf 0.50(methanol:chloroform=1:9);

NMR (CDCl$_3$): δ 8.13(s, 1H), 5.66 (dt, J=15, 6 Hz, 1H), 5.40 (dd, J=15, 9 Hz, 1H), 3.50-3.25 (m, 2H), 3.15-3.05 (m, 1H), 3.00-2.50 (m, 1H), 2.50-2.25 (m, 4H), 2.23 (d, J=6 Hz, 2H), 2.20-2.00 (m, 3H), 2.00-1.85 (m, 1H), 1.85-1.60 (m, 3H), 1.21 (s, 3H).

Example 21

Methyl 2-[(2-{(1R,5S)-2-oxo-5-[(1E,4S)-7,8,8-trifluoro-4-hydroxy-4-methyl-1,7-octadien-1-yl]-3-cyclopenten-1-yl}ethyl)thio]-1,3-thiazole-4-carboxylate (Compound 21)

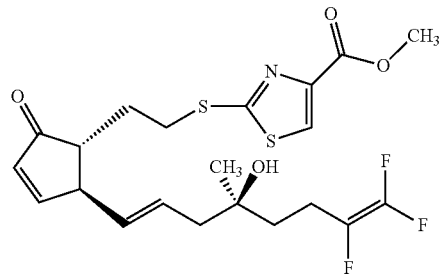 [SMILES: COC(=O)c1csc(SCC[C@H]2C(=O)C=C[C@@H]2/C=C/C[C@@](C)(O)CCC(F)=C(F)F)n1]

TLC: Rf 0.38(ethyl acetate:hexane=1:1);

NMR (CDCl$_3$): δ 1.19(s, 3H), 1.60-1.80 (m, 2H), 1.95 (m, 1H), 2.23 (d, J=7.5 Hz, 2H), 2.20-2.48 (m, 4H), 3.30 (m, 1H), 3.44-3.58 (m, 2H), 3.91 (s, 3H), 5.48 (dd, J=15.0, 8.4 Hz, 1H), 5.84 (dt, J=15.0, 7.2 Hz, 1H), 6.17 (dd, J=5.7, 2.1 Hz, 1H), 7.49 (dd, J=5.7, 2.4 Hz, 1H), 8.01 (s, 1H).

Example 22

β-cyclodextrin clathrate of sodium 2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylate (mixing molar ratio=1:3)

The sodium salt of compound 17 (8.12 mg) and β-cyclodextrin (56.88 mg) were weighed and dissolved in purified water (5 mL). The solution was allowed to stand for 30 min; freeze-dried; and dried under reduced pressure at room temperature overnight to obtain the title compound (64.8 mg).

NMR (D$_2$O)

Peaks from sodium 2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylate: 7.81(s, 1H), 5.57-5.40 (m, 2H), 3.26-3.19 (m, 2H), 2.49 (m, 1H), 2.35-1.98 (m, 9H), 1.83 (m, 1H), 1.64 (m, 1H), 1.55-1.46 (m, 2H), 1.01 (s, 3H).

Peaks from β-cyclodextrin: 4.91(d, J=3.6 Hz, 1H), 3.81-3.63 (m, 4H), 3.51-3.41 (m, 2H).

BIOLOGICAL EXAMPLES

It was demonstrated by the following experiments that the compound of the present invention is a compound which has activity to contract bladder and relax the urethra; causes less side effects; and has good pharmacokinetics such as oral absorbency.

Additionally, the following comparative experiments were also conducted to demonstrate that the compound of the present invention has better pharmacokinetics such as safety and oral absorbency than the compounds described in the prior art documents.

Comparative compound A: 2-[(2-{(1R,2R)-2-[(1E,4S)-4-hydroxy-4,7-dimethyl-1,7-octadien-1-yl]-5-oxocyclopentyl}ethyl)thio]-1,3-thiazole-4-carboxylic acid (the 4S-form of compound 18-6 described in the pamphlet of International Publication No. WO 2006/129788)

Comparative compound B: 2-[(2-{(1R,2R)-2-[(1E,4S)-4-hydroxy-4-methyl-1-nonen-1-yl]-5-oxocyclopentyl}ethyl)thio]-1,3-thiazole-4-carboxylic acid (the compound 17-1 described in the pamphlet of International Publication No. WO 2006/129788)

Comparative compound C: 2-[(2-{(1R,5R)-2-oxo-5-[(1E,4S)-8,8,8-trifluoro-4-hydroxy-4-methyl-1-octenyl]cyclopentyl}ethyl)thio]-1,3-thiazole-4-carboxylic acid (the 4S-form of the compound 18-1 described in the pamphlet of International Publication No. WO 2006/129788)

Comparative compound D: 2-[(2-{(1R,2R)-2-[(1E,4S)-4-hydroxy-4-methyl-1,7-octadien-1-yl]-5-oxocyclopentyl}ethyl)thio]-1,3-thiazole-4-carboxylic acid (the 4S-form of the compound 32 described in the pamphlet of International Publication No. WO 2006/129788)

Comparative compound E: 2-[(2-{(4S)-2-oxo-4-[(1E,4S)-8,8,8-trifluoro-4-hydroxy-4-methyl-1-octenyl]-1,3-oxazolidin-3-yl}ethyl)sulfanyl]-1,3-thiazole-4-carboxylic acid (the compound 65-2 described in the pamphlet of International Publication No. WO2005/053707)

(1) Evaluation of the Activity to Contract the Bladder Detrusor and Relax the Urethral Sphincter <Construction of Incised Specimens>

Rats were anesthetized with pentobarbital, followed by abdominal incision to remove the bladders and the urethras. The bladder bodies were cut in the longitudinal direction to prepare strip specimens with a size of about 10×3 mm. Additionally, each of the urethras was also cut in the longitudinal direction to prepare specimens with a size of about 10×3 mm. The prepared specimens were suspended in Krebs buffer (37° C., 5 mL), which was aerated with a mixed gas of 95% $O_2$ and 5% $CO_2$. The tension values of the specimens were measured using a Magnus system equipped with an isometric transducer and an amplifier, and the measured values were recorded on a computer via a data collection system.

<Effects of Compounds on Bladders>

The specimens were suspended with a load of about 0.5 g. More than 1 hr later, potassium chloride (100 mmol/L) was added and the maximal contraction response was observed. After washing with Krebs buffer, the specimens were suspended with a load of about 0.5 g for stabilization. A potassium chloride solution (7.5 mmol/L) was added to induce the contraction of the specimens. After the contraction-inducing response was stabilized, the test compound was added in a cumulative manner and the response was observed before and after the treatment with the drug.

<Effect of Compounds on Urethras>

The specimens were suspended with a load of about 0.5 g. More than 1 hr later, potassium chloride (100 mmol/L) was added to the suspension and the maximal contraction response was observed. After washing with Krebs buffer, the specimens were suspended with a load of about 0.5 g for stabilization. Thereafter, a phenylephrine (100 μmol/L) was added to the suspension to induce the contraction of the specimens. After stabilization of the contraction-inducing response, the test compound was added in a cumulative manner and the response was observed before and after the treatment of the drug.

<Results>

The results are given in Tables 1 and 2.

TABLE 1

| | Contractility of the bladder detrusor according to the compound concentration treated (% of 7.5 mmol/L KCl) | | | | | |
|---|---|---|---|---|---|---|
| | 0 nmol/L | 1 nmol/L | 10 nmol/L | 100 nmol/L | 1 μmol/L | 10 μmol/L |
| Vehicle (n = 11) | 3 | 0 | −4 | −12 | −14 | −15 |
| Compound 17 (n = 4) | 3 | −2 | 23 | 100 | 180 | 259 |

TABLE 2

| | Contractility of the urethral sphincter according to the compound concentration treated (% of phenylephrine) | | | | | |
|---|---|---|---|---|---|---|
| | 0 nmol/L | 1 nmol/L | 10 nmol/L | 100 nmol/L | 1 μmol/L | 10 μmol/L |
| Vehicle (n = 11) | −4 | −11 | −13 | −25 | −38 | −44 |
| Compound 17 (n = 4) | 5 | −2 | −9 | −36 | −83 | −89 |

From the above experimental results, the compound 17 contracted the bladder detrusor and relaxed the urethral sphincter. Therefore, the compound of the present invention acts on the bladder and urethra to ameliorate bladder contraction dysfunction and urethral relaxation dysfunction, which is effective for underactive bladder.

(2) Measurement of Residual Urinary Volumes and Bladder Capacities in Underactive Bladder Models <Construction of Animal Models and Indwelling of Catheters>

The underactive bladder models were constructed in accordance with the following procedure. Female Wistar rats (8 to 9 weeks age) were anesthetized by intraperitoneal administration of Somnopentyl (40 mg/kg), followed by dorsal shaving, and fixed in abdominal positions. Each of the dorsal areas was disinfected with chlorhexidine gluconate (5% hibitane liquid). The waist area was median-incised to expose the spinal column. After excision of the fifth lumbar spinous process, a silicone rubber was inserted into the sixth lumbar direction from a hole bored by a mini drill. For the purpose of avoiding infections, after completion of the surgical operation, benzylpenicillin potassium (25000 U/0.25 mL/body) was added dropwise to the incised area. The muscle and skin of the incised area were sutured with silk threads, and iodine tincture was applied to the sutured area. After the operation, maintenance of voiding was carried out by manual compressions three times daily. For the purpose of avoiding infections, potassium penicillin G (1.25 units/body) was administered subcutaneously. More than 5 days prior to cystometric evaluation, a catheter for cystometrogram was indwelled in the bladder. Anesthesia with sodium pentobarbital (40 mg/kg by intraperitoneal administration) and incision along the midline of the abdomen were carried out, followed by incision of the apex of the bladder. A catheter for cystometrogram filled with physiological saline was inserted into the bladder from a hole of the apical area, and fixed by ligation using silk suture threads. The other end of the catheter was fixed to the dorsal hypoderm. The incised areas of the lower back and abdomen were sutured with silk threads. Viccillin S500 (Meiji Co., Ltd., 10 mg titer/0.1 mL distilled water/rat) was infused into the muscle of the rump.

<Preparation of Cystometry>

The rats were anesthetized with ether and housed in a Bollmann cage 2 weeks after the construction of the models. To the front end of each of the bladder catheters, a pressure transducer via a three-way cock was connected, and the intravesical pressure was recorded using a strain pressure amplifier•recorder. One end of the three-way cock was connected to an intravesical instillation syringe mounted in an infusion pump, and the other end was connected to an extension tube filled with physiological saline, which was used for the discharge of residual urine. The treated rats were left until the rats came out from under the anesthesia.

<Experimental Method>

Injectable water (vehicle group) and the test compound (5 mg/kg) were orally administered. After 1 hr, physiological saline was perfused into the bladder at a flow rate of 2 mL/h and voiding parameters (bladder capacity and residual urinary volume) were measured. After 1 hr of perfusion and immediately after urination, the perfusion was stopped and residual urine in the bladder was removed. Voiding parameters were calculated for each cystometry. With regard to the residual urinary volumes, values of the vehicle group and the group wherein the test compound was administered were compared. With regard to the bladder capacities, values of the normal group and the test group wherein the test compound was administered were compared.

<Results>

Figure 2:
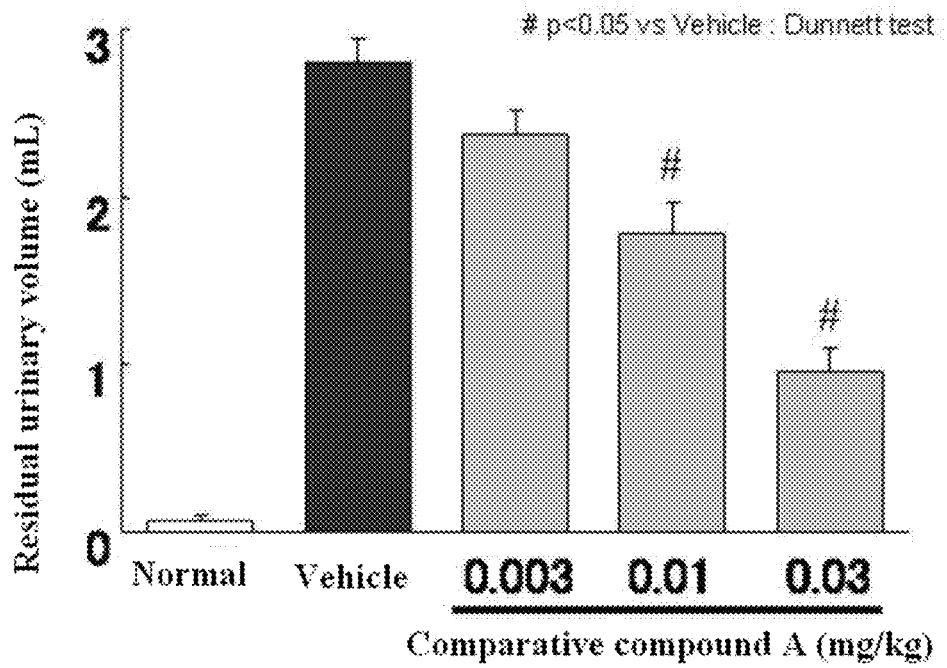
FIG. 2 shows the effects of a comparative compound on residual urinary volume (upper graph) and bladder capacity (lower graph) in underactive bladder models.
Figure 2:
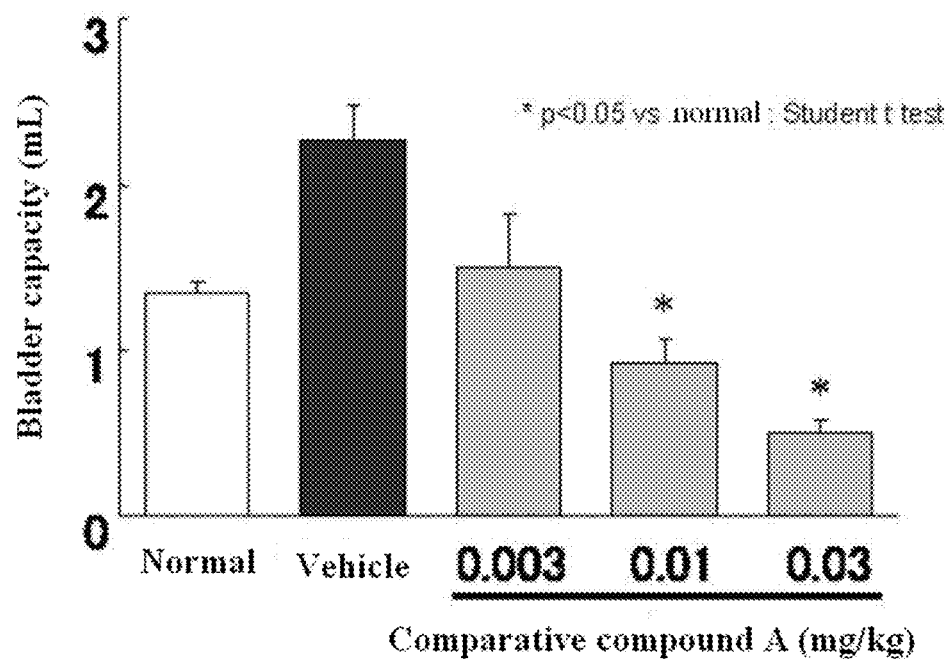

The results are shown in FIGS. 1 and 2. Compound 17 had no effect on the bladder capacity at a dose (0.01 mg/kg) producing a significant reduction in the residual urinary volume of the underactive bladder models. In contrast, comparative compound A produced a significant decrease in bladder capacity at an effective dose (0.01 mg/kg).

It is thought that a reduction in bladder capacity than the normal level leads to a storage symptom wherein urine cannot be stored, resulting in frequent urination, which is a side effect on the urinary system.

From the results, the compound of the present invention is effective as a therapeutic agent for underactive bladder and does not cause side effects on the urinary system at an effective dose.

(3) Measurement of Blood Pressures and Heart Rates in Normal Rats

<Measurement Method>

The blood pressures and heart rates of female Wistar rats were measured in accordance with the following procedure. On the day of measurement, indwelling of catheters for blood pressure•heart rate measurement was carried out under anesthesia with ether. The back of the neck of each rat was incised; a feeding catheter (Atom Medical Corporation) filled with heparinized physiological saline was introduced from the back of the neck; the catheter was inserted into the common carotid artery; and the surgical incision was closed. The measurements were carried out in a Bollmann cage under the conscious state, and the evaluations were carried out after confirming that the individual parameters were stabilized. After confirming the stabilization of blood pressure and heart rate, the test compound which was prepared using injectable water containing equimolar NaOH was orally administered at a dose of 5 mL/kg.

The catheter drawn from the back of the neck was connected to a pressure transducer (DX-200, NIHON KOHDEN CORP.), and the blood pressures and heart rates were measured using an amplifier for pressure measurement (Gould Instrument). The blood pressures and heart rates were recorded using a recorder (LINEARCORDERWR3320, GRAPHTEC). For each individual, rates of increase and decrease in average blood pressure and heart rate before administration and 30, 60, 120, and 180 min after administration were calculated with respect to the values of each individual before administration. Changes in blood pressure and heart rate before and after administration of the test compound were evaluated.

<Results>

Figure 3:
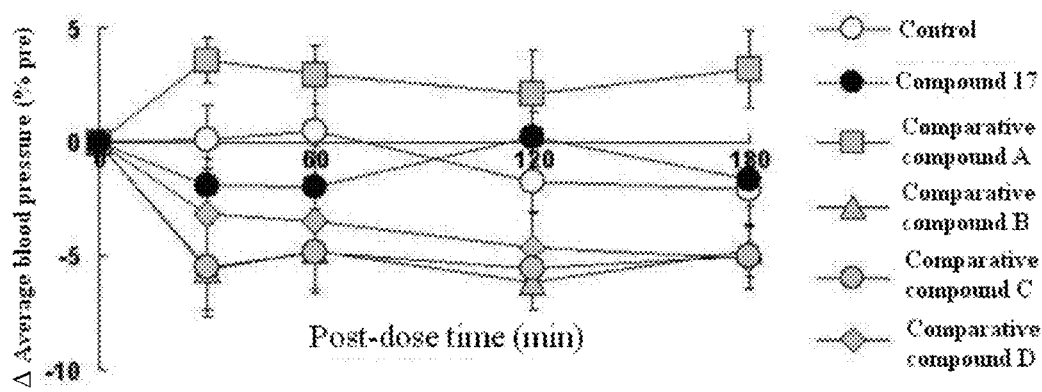
FIG. 3 shows the effects of the compound of the present invention and a comparative compound in blood pressure in normal rats.
Figure 4:
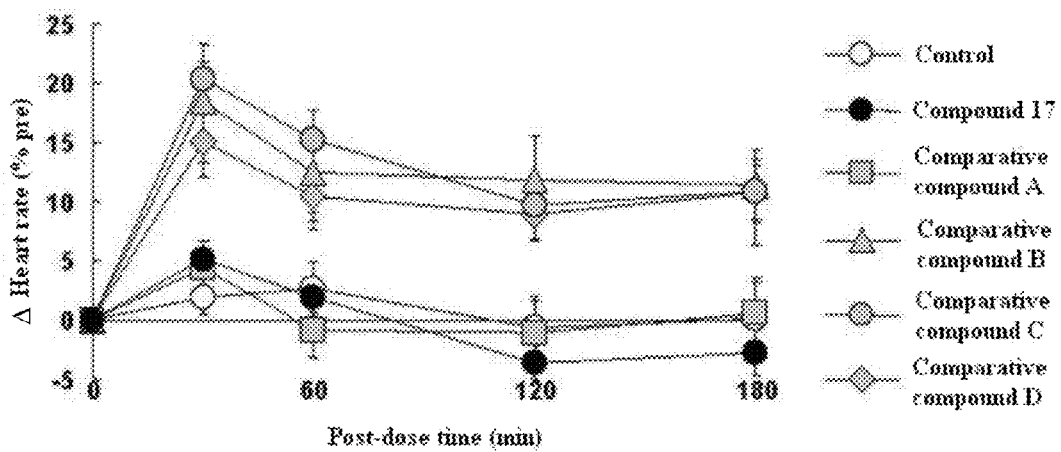
FIG. 4 shows the effects of the compound of the present invention and a comparative compound in heart rate in normal rats.

FIGS. 3 and 4 shows the results obtained after administration of the compound of the present invention (0.3 mg/kg) and the comparative compound (0.3 mg/kg).

The compound 17 had no effect on the blood pressure at a dose of concentration of 0.3 mg/kg. Furthermore, the compound 17 had no effect on the blood pressure even at a dose of concentration of 1 mg/kg. In contrast, the comparative compound A showed a tendency to increase the blood pressure at a dose of concentration of 0.3 mg/kg, and to increase an about 10% in blood pressure at a dose of concentration of 1 mg/kg. Furthermore, comparative compound B, comparative compound C and comparative compound D showed a tendency to decrease the blood pressure at a dose of concentration of 0.3 mg/kg.

The compound 17 had no effect on the heart rate at a dose of concentration of 0.3 mg/kg. In contrast, the comparative compound B, the comparative compound C and the comparative compound D produced an about 20% increase in heart rate at a dose of concentration of 0.3 mg/kg.

The above results showed that the comparative compounds posses the risk of influencing the blood pressure and heart rate, whereas the compound of the present invention has little effect on the blood pressure and heart rate.

Therefore, the compound of the present invention has little risk of side effects on the circulatory system.

(4) Blood Pressure and Heart Rate Measurement in Hypertensive Rats

The blood pressures and heart rates of male spontaneously hypertensive rats were measured. On the day of measurement, indwelling of catheters for blood pressure•heart rate measurement and subject substance administration was carried out under anesthesia with ether. The back of the neck of each rat was incised, a feeding catheter (Atom Medical Corporation) filled with heparinized physiological saline was introduced from the back of the neck; the catheter was inserted into the common carotid artery and internal jugular vein; and the surgical incision was closed. The measurements were conducted in a Bollmann cage under the conscious state and evaluations were carried out after confirming that the individual parameters were stabilized. After confirming the stabilization of blood pressure and heart rate, the test compound was continuously administered intravenously at a flow rate of 5 mL/kg/h for 30 min.

The catheter drawn from the back of the neck was connected to a pressure transducer (DX-200, NIHON KOHDEN CORP.), and the blood pressures and heart rates were measured using a blood pressure amplifier (Gould instrument). The blood pressures and heart rates were recorded on recording paper using a recorder (LINEARCORDER WR3320, GRAPHTEC). The blood pressures and heart rates were converted into values on the recording paper before administration and 2.5, 5, 10, 15, 30, 45 and 60 min after administration. For each individual, rates of increase and decrease in the parameters were evaluated relative to the value before administration (value at 0 min).

<Results>

Figure 5:
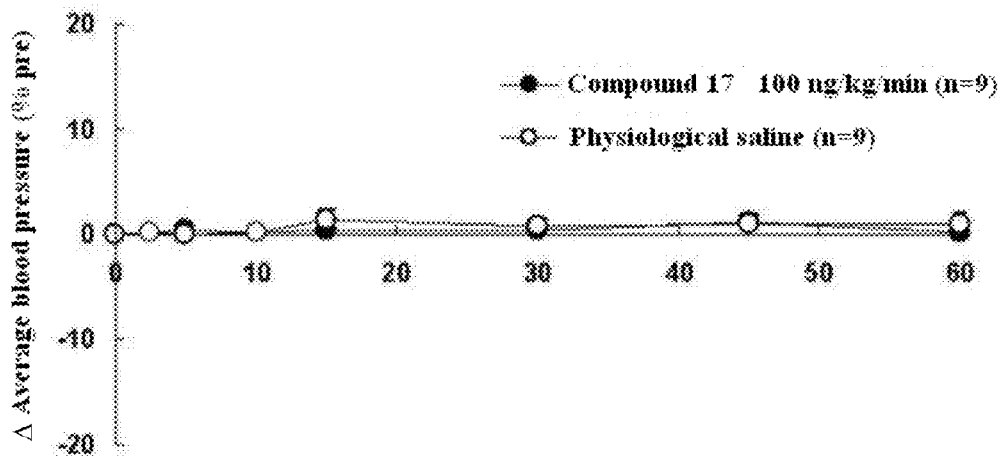
FIG. 5 shows the effects of the compound of the present invention on blood pressure in hypertensive rats.
Figure 6:
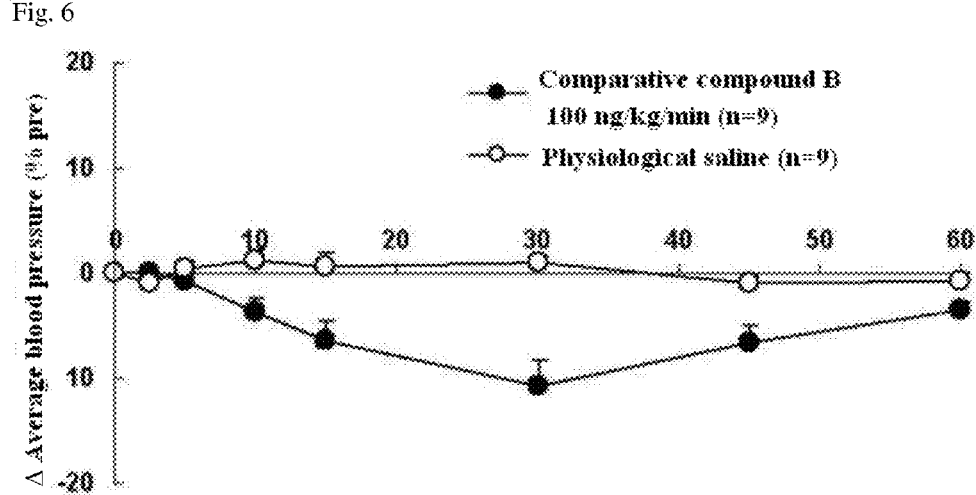
FIG. 6 shows the effects of a comparative compound on blood pressure in hypertensive rats.

The results are shown in FIGS. 5 and 6.

Compound 17 had no effect on the blood pressure. In contrast, comparative compound B reduces an about 10% blood pressure in administion at a dose of 100 ng/kg/min. Additionally, it reduces an about 25% blood pressure inadministion at a dose of 300 ng/kg/min.

From the results, the compound of the present invention has low risk of side effects on the circulatory system in patients suffering from circulatory illness such as hypertension.

(5) Digestive Symptoms

Using male rats, aged 6 weeks, general states of the rats were observed after repeating oral administration of the test compound at a dose of 0.1 mg/kg for 4 days. To a control, injectable water which is a medium was administered.

<Results>

No digestive symptoms such as soft feces were observed in the groups administered with the compound 17. In contrast, soft feces were observed in the groups administered with the comparative compound C from the first day after administration.

Thus, the compound of the present invention is safe without causing side effects on the digestive system.

(6) Evaluation of Membrane Permeability of Drugs (Oral Absorbability)

The permeability of the drugs through artificial membranes was measured by parallel artificial membrane permeability assay (PAMPA) under the following conditions. For the measurements, a PAMPA system (pION) was used. The membrane permeability was evaluated by measuring membrane permeability coefficients at three pH values and summing the values (PAMPA(SUM)(cm/sec)).

Lipid membrane: GIT-0 (pION)
Wavelength: 190-498 nm
Incubation time: 4 hr
Incubation temperature: 25° C.
Donor: 5% DMSO-containing buffer
pH: 3 points of 5.0, 6.2 and 7.4
Compound concentration: 50 µmol/L <Results>

The membrane permeability coefficients of compound 17 was 59.3 cm/sec which showed very good membrane permeability. On the other hand, membrane permeability coefficients of comparative compound E was 0.6 cm/sec and it could be known that membrane permeability was low.

The results suggest that the compound of the present invention has good membrane permeability and is superior in oral absorbability.

(7) Evaluation of Systemic Clearance

Equimolar sodium hydroxide and injectable distilled water were added to each of the test compounds to prepare a 1 mg/mL aqueous solution. The aqueous solution was diluted with physiological saline until the concentration reached 0.001 mg/mL and was rapidly administered at a dose of 0.001 mg/mL/kg to cynomolgus monkey through the cephalic vein. Via heparinized syringes, 2 min, 5 min, 15 min, 30 min, 1 hr, 2 hr, 4 hr, 6 hr, 8 hr and 24 hr after administration, blood was drawn from the cephalic vein (non-administered sites). After centrifugation, blood plasma was sampled and stored at $-80°$ C. before pretreatment. The blood plasma was pretreated by mixing with acetonitrile and centrifuging to remove proteins followed by measurement by LC/MS/MS. Changes of concentration in blood plasma was analyzed using WinNonlin4.0.1 to evaluate the systemic clearance of the test compound.

<Results>

The systemic clearance of the compound 17 was 3.6 mL/min/kg, which showed slow loss from the body and continuous drug action efficacy. In contrast, the systemic clearance of the comparative compound D was 23.9 mL/min/kg, which was clearly higher clearance than that of the compound 17 and very fast loss from the body in comparison with the compound 17 was shown.

(8) Stability Evaluation in Lyophilized Liver Cells

KHEM5100 medium which includes human lyophilized liver cells after dissolving (final concentration of living cells: $1\times10^6$ cells/mL) and the test compound (acetonitrile or methanol solution, final concentration ≤1%) was incubated at 37° C. Immediately after reaction and with the passage of reaction time, some portions were sampled from the medium.

The concentrations of the test compound in the samples were measured by LC/MS/MS. The residual rate of the test compound relative to immediately after reaction was calculated by the following equation:

Residual rate=the concentration of the test compound in the sample after reaction/the concentration of the test compound in the sample immediately after reaction×100(%)

The residual rates were plotted on a single logarithmic scale against reaction time to calculate loss rate constants. The test was repeated (n=2), and the obtained values were averaged.

<Results>

The results are shown below.

TABLE 3

|  |  | Reaction time (h) | | | |
| --- | --- | --- | --- | --- | --- |
|  |  | 0 | 0.5 | 1 | 2 |
| Residual rate | Compound 17 | 100 | 111 | 101 | 82.2 |
|  | Comparative compound B | 100 | 91.5 | 78.1 | 62.3 |

The residual rate of comparative compound B was 80% or less 1 hr after reaction and about 60% 2 hr after reaction. In contrast, the residual rate of compound 17 was 100% 1 hr after reaction and 80% or more even 2 hr after reaction.

The results demonstrate high stability of the compound of the present invention against metabolism in the liver.

(9) Effects on Cardiac Function

Cynomolgus monkeys were anesthetized with pentobarbital (at an initial dose of 20-30 mg/kg by intravenous administration; at a dose of 4-5 mg/kg/hr by intravenous continuous administration). A tracheal tube was inserted and experiments were carried out under artificial respiration (fresh air+pure oxygen, ventilatory volume: 10-15 mL/kg, ventilation frequency: 10-15 times/min). In the right lying position, the left thorax was opened between the fourth and fifth intercostal spaces. The common carotid artery (the origin of the left anterior descending artery or circumflex branch) and the origin of the ascending main artery were peeled off and transducers for blood flow measurement were located there. The blood flow rates were measured using an electronic blood flowmeter or an ultrasonic blood flowmeter. The blood pressures were measured using a pressure transducer in a state where a catheter was inserted into the right femoral artery. The left ventricular internal pressure was measured in a state where a catheter was inserted from the left carotid artery into the left ventricle. The electrocardiogram was measured using needle electrodes installed in the right armpit and the left thorax. After catheters for administration were inserted into the right and left cephalic veins and femoral veins, the test compound, pentobarbital (under anesthesia) or an aqueous solution (SOLITA T3 containing 1.2% $NaHCO_3$) were administered therethrough. The test compound was continuously administered intravenously 30 min using a continuous infusion system. The blood pressure, left ventricular internal pressure, blood flow rate through the coronary artery and electrocardiogram data were simultaneously inputted to a PowerLab system (LabChart6, AD instruments) to measure/calculate average blood pressure, heart rate, average blood flow rate through the coronary artery, beat volume, stroke volume (beat volume/heart rate), maximum first deviation of the left ventricular internal pressure, total peripheral blood vessel resistance (average blood pressure/beat volume), cardiac performance (average blood pressure×beat volume) and double product (systolic arterial pressure×heart rate), which is indicative of myocardial oxygen consumption.

The averages of all evaluation parameters for 1 min were obtained before administration, immediately after administration, and 10 min, 20 min and 30 min after administration, and changes of the averages relative to the value measured before administration which is defined as 100% were calculated.

<Results>

Figure 7:
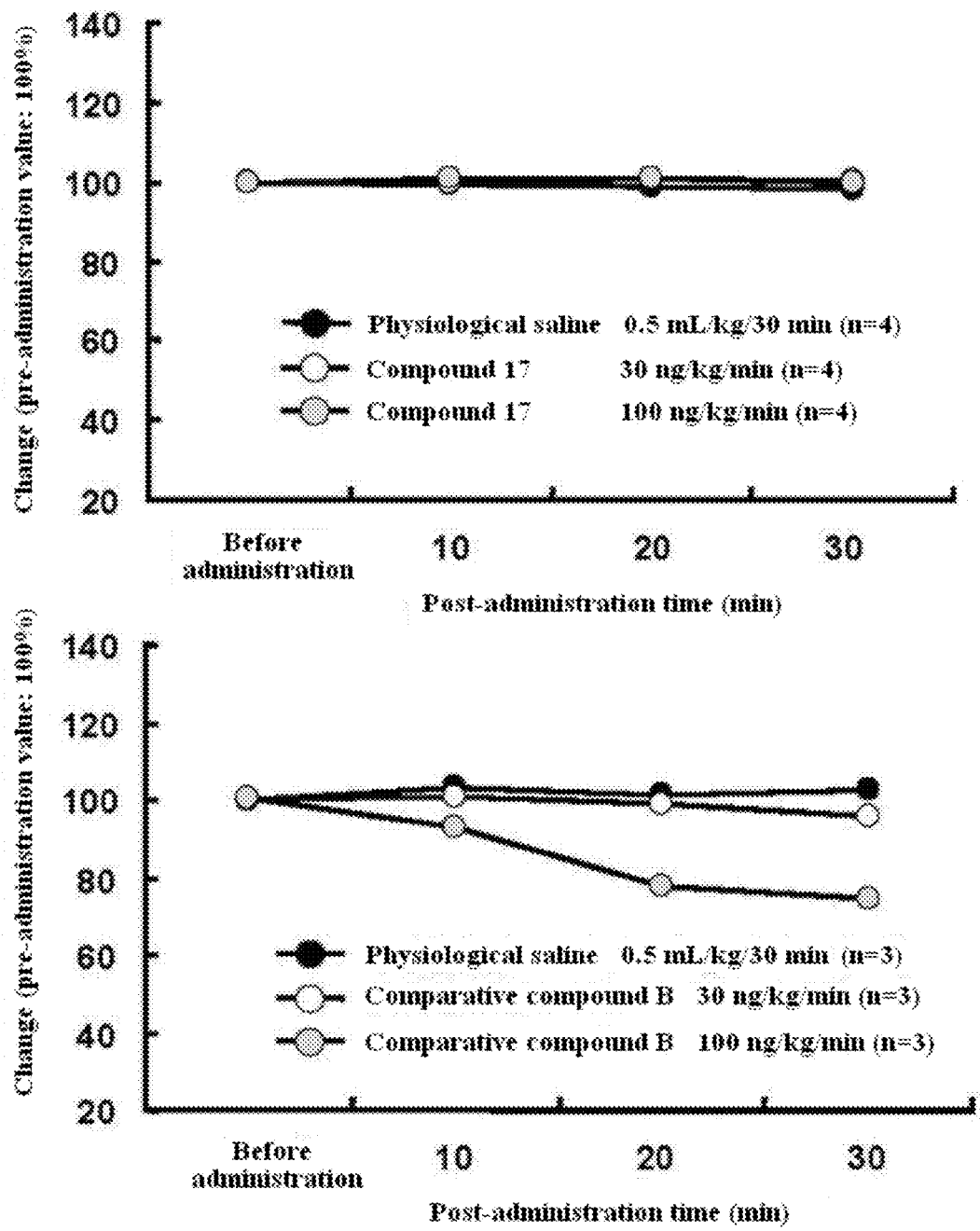
FIG. 7 shows the cardiac performance of the compound of the present invention (upper graph) and a comparative compound (lower graph) in cynomolgus monkeys.
Figure 8:
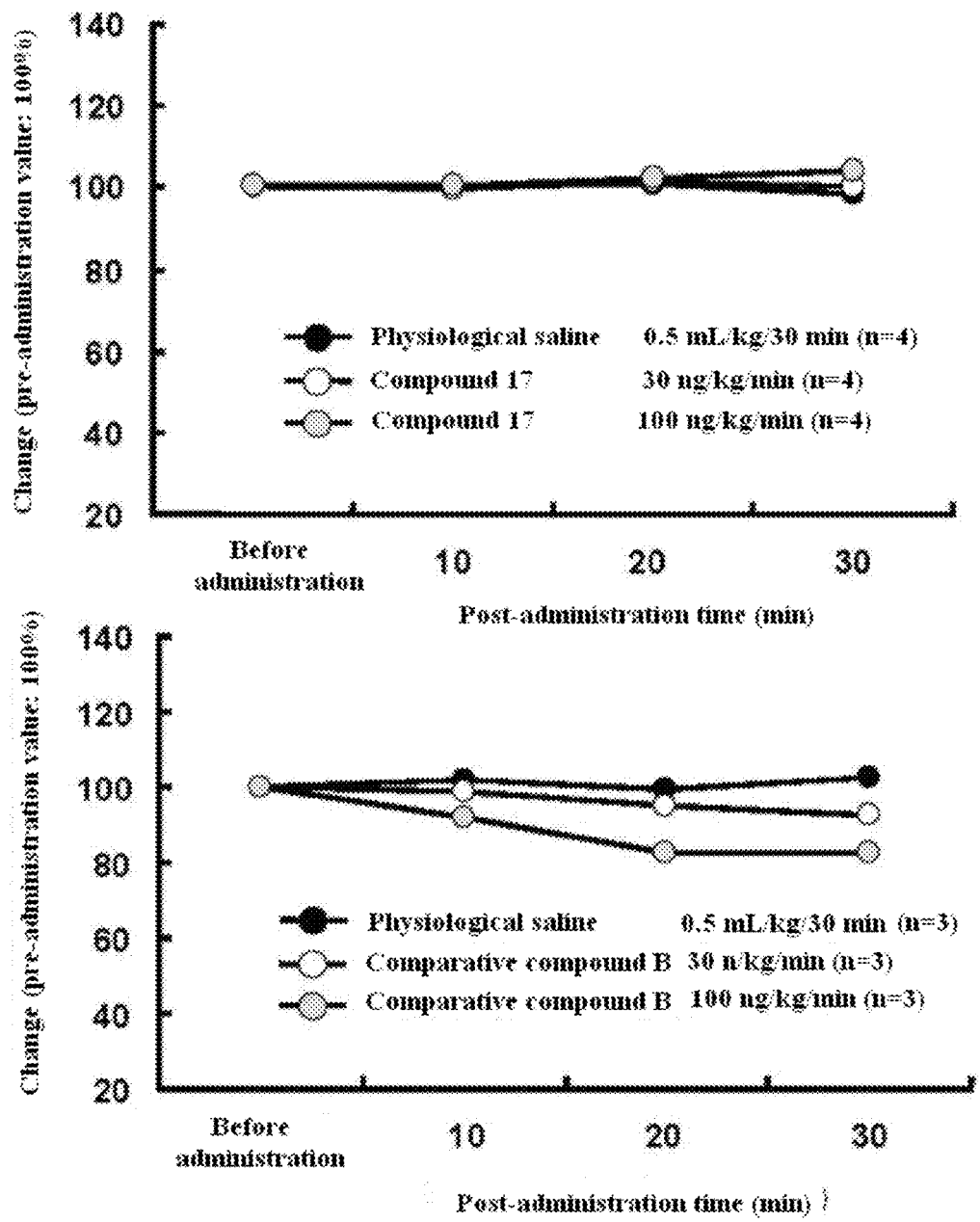
FIG. 8 shows the double products of the compound of the present invention (upper graph) and a comparative compound (lower graph) in cynomolgus monkeys.

The cardiac performance and double products are shown in FIGS. 7 and 8. The compound 17 did not affect the cardiac performance and double product at doses of 30 ng/kg/min and 100 ng/kg/min. Additionally, the compound 17 did not affect the other cardiac function parameters, including the blood flow rate through the coronary artery. In contrast, the comparative compound B had an inhibitory effect on the cardiac functions.

From the above, the compound of the present invention is a safe compound which does not affect cardiac functions.

(10) Effects on Urinary Excretion Dysfunction Models

<Construction of Animal Models>

Urinary excretion dysfunction models were constructed in accordance with the following procedure. After anesthesia of cynomolgus monkeys, the region from the suprapubic area to the abdominal area was shaved, followed by fixing in a dorsal position. The shaved region was disinfected and the four legs were fixed. Using an electrosurgical knife, the skin region from the suprapubic area to the umbilical area and the peritoneal membrane were sequentially incised, followed by damage to the pelvic nerve and removal of the uterus. After the surgical operation, viccillin-containing physiological saline was added dropwise to the incised area. The peritoneal membrane and skin of the incised area were sutured with silk threads and disinfected. Viccillin was administered for 7 consecutive days after surgery. Meloxicam was administered once daily for 7 consecutive days to manage pain in the perioperative period.

<Experimental Method>

The cynomolgus monkeys were seated on monkey chairs, followed by retention of the hands and legs with strings. Injectable water was administered orally, and physiological saline and the test compound (60 ng/kg/h) were continuously administered intravenously to allow urination freely. The maximal urinary flow rate was measured using a urine weighing sensor.

<Results>

In the urinary excretion dysfunction model, the compound 17 showed a 61% improvement in maximal urinary flow rate over the vehicle group. In contrast, comparative compound B and comparative compound D showed only 27% and 36% improvement in maximal urinary flow rate over the vehicle group.

From the results, it was shown that the compound of the present invention is very effective in promoting urination.

The results obtained in Biological Examples (1) to (10) reveal that the compound of the present invention has a bladder contracting activity and a urethral relaxing activity and high promoting urination activity. Additionally, the compound of the present invention is a compound which is superior in safety and can avoid all risk of side effects on the urinary system, circulatory system and digestive system, which could not be achieved by any compounds described in prior art. Furthermore, the compound of the present invention has excellent pharmacokinetics including oral absorbability and metabolic stability.

FORMULATION EXAMPLES

Formulation Example 1

The compound 17 (5.0 g), calcium carboxymethyl cellulose (20 g), magnesium stearate (10 g) and microcrystalline cellulose (920 g) were mixed by a general method, followed by compression to produce 10,000 tablets wherein 0.5 mg of the active ingredient was present in each of the tablets.

Formulation Example 2

The compound 17 (2.0 g), mannitol (500 g) and distilled water (10 L) were mixed by a general method, followed by sterilization by a general method. 1 mL of the solution was filled in a vial and frozen-dried by a general method. A total of 10,000 vials were obtained wherein 0.2 mg of the active ingredient was present in each of vials.

INDUSTRIAL APPLICABILITY

The compound of the present invention has a contracting activity of bladder detrusor and a relaxing activity of urethral sphincter. Therefore, the compound of the present invention can ameliorate bladder contraction dysfunction and/or urethral relaxation dysfunction and is particularly effective as an agent for preventing and/or treating underactive bladder. Additionally, the compound of the present invention is effective as an agent for ameliorating various symptoms associated with underactive bladder. Furthermore, the compound of the present invention is very safe and exhibits excellent pharmacokinetics, including oral absorbability etc. Therefore, the compound of the present invention is very useful as a medicament.

The invention claimed is:

1. A method for contracting the bladder detrusor and relaxing the urethral sphincter comprising administering a compound represented by formula (I):

wherein ╲╲╲ represents an α-configuration;

▲ represents a β-configuration; and

╱ represents an α-configuration, a β-configuration or an arbitrary mixture thereof, a salt thereof, a solvate thereof, a prodrug thereof, a mixture with a diastereomer thereof in an arbitrary ratio, or a cyclodextrin clathrate thereof.

2. A method for treating and/or ameliorating bladder contraction dysfunction and/or urethral relaxation dysfunction comprising administering a compound represented by formula (I):

wherein ╲╲╲ represents an α-configuration;

▲ represents a β-configuration; and

╱ represents an α-configuration, a β-configuration or an arbitrary mixture thereof, a salt thereof, a solvate thereof, a prodrug thereof, a mixture with a diastereomer thereof in an arbitrary ratio, or a cyclodextrin clathrate thereof.

3. The method of claim 2, wherein the bladder contraction dysfunction and/or the urethral relaxation dysfunction is underactive bladder.

* * * * *